(12) United States Patent
Purdy et al.

(10) Patent No.: US 10,470,781 B2
(45) Date of Patent: Nov. 12, 2019

(54) MEDICAL DEVICES FOR TREATING HARD TISSUES AND RELATED METHODS

(71) Applicant: DFine, Inc., South Jordan, UT (US)

(72) Inventors: Craig Purdy, Sunnyvale, CA (US);
Dan Balbierz, Redwood City, CA (US);
Nate Shirley, Pleasant Grove, UT (US);
Jose Galdos, San Jose, CA (US)

(73) Assignee: DFine, Inc., South Jordan ( * ) Notice: Subject to any disclaimer, the term of this patent is extended or adjusted under 35 U.S.C. 154(b) by 181 days.

(21) Appl. No.: 15/836,125

(22) Filed: Dec. 8, 2017

(65) Prior Publication Data

US 2018/0161046 A1 Jun. 14, 2018

Related U.S. Application Data

(60) Provisional application No. 62/432,182, filed on Dec. 9, 2016, provisional application No. 62/432,217, filed on Dec. 9, 2016.

(51) Int. Cl.
*A61B 17/00* (2006.01)
*A61B 17/16* (2006.01)
(Continued)

(52) U.S. Cl.
CPC ...... *A61B 17/1631* (2013.01); *A61B 17/1659* (2013.01); *A61B 17/1671* (2013.01);
(Continued)

(58) Field of Classification Search
CPC combination set(s) only.
See application file for complete search history.

(56) References Cited

U.S. PATENT DOCUMENTS 2,688,329 A 9/1954 Wallace
3,140,623 A 7/1964 Hoose
(Continued)

FOREIGN PATENT DOCUMENTS

CA 2785207 7/2011
CN 88203061 11/1988
(Continued)

OTHER PUBLICATIONS

US 7,063,700 B2, 06/2006, Michelson (withdrawn)
(Continued)

*Primary Examiner* — Sameh R Boles
(74) *Attorney, Agent, or Firm* — Stoel Rives LLP

(57) ABSTRACT

Medical devices such as osteotomes are provided. The medical device may include inner and outer members that form a working end portion. Distal end portions of the inner and outer members can cooperate to allow deflection of the working end portion. Medical devices including indicators are also provided. The indicator may communicate a direction of deflection of the working end portion to a practitioner. Additionally, medical devices including torque release mechanisms are provided. The torque release mechanism may uncouple a first portion of the medical device from a second portion of the medical device when an amount of torque applied to the medical device exceeds a predetermined value. The torque release mechanism may limit damage to components of the medical device during use of the medical device.

19 Claims, 10 Drawing Sheets

(51) Int. Cl.
  *A61B 17/34* (2006.01)
  *A61B 90/00* (2016.01)
  *A61B 18/14* (2006.01)
  *A61B 17/17* (2006.01)

(52) U.S. Cl.
  CPC .......... *A61B 17/3421* (2013.01); *A61B 90/03* (2016.02); *A61B 17/1642* (2013.01); *A61B 17/1644* (2013.01); *A61B 17/1707* (2013.01); *A61B 17/3472* (2013.01); *A61B 18/148* (2013.01); *A61B 2017/00309* (2013.01); *A61B 2017/00455* (2013.01); *A61B 2090/031* (2016.02)

(56) References Cited

U.S. PATENT DOCUMENTS

| | | |
|---|---|---|
| 3,228,400 A | 1/1966 | Armao |
| 3,503,385 A | 3/1970 | Stevens |
| 3,625,200 A | 12/1971 | Muller |
| 3,664,344 A | 5/1972 | Bryne |
| 3,794,039 A | 2/1974 | Kollner et al. |
| 3,908,637 A | 9/1975 | Doroshow |
| 4,033,331 A | 7/1977 | Guss et al. |
| 4,131,597 A | 12/1978 | Bluethgen et al. |
| 4,236,520 A | 12/1980 | Anderson |
| 4,276,880 A | 7/1981 | Malmin |
| 4,294,251 A | 10/1981 | Grennwald et al. |
| 4,337,773 A | 7/1982 | Raftopoulos et al. |
| 4,386,717 A | 6/1983 | Koob |
| 4,399,814 A | 8/1983 | Pratt, Jr. et al. |
| 4,411,266 A | 10/1983 | Cosman |
| 4,456,017 A | 6/1984 | Miles |
| 4,473,077 A | 9/1984 | Noiles |
| 4,476,861 A | 10/1984 | Dimakos et al. |
| 4,578,061 A | 3/1986 | Lemelson |
| 4,586,923 A | 5/1986 | Gould et al. |
| 4,595,006 A | 6/1986 | Burke et al. |
| 4,619,263 A | 10/1986 | Frisbie et al. |
| 4,627,434 A | 12/1986 | Murray |
| 4,641,654 A | 2/1987 | Samson et al. |
| 4,653,489 A | 3/1987 | Tronzo |
| 4,668,295 A | 5/1987 | Bajpai |
| 4,719,968 A | 1/1988 | Speros |
| 4,722,948 A | 2/1988 | Sanderson |
| 4,731,054 A | 3/1988 | Billeter et al. |
| 4,742,817 A | 5/1988 | Kawashima et al. |
| 4,747,840 A | 5/1988 | Ladika et al. |
| 4,748,969 A | 6/1988 | Wardle |
| 4,784,638 A | 11/1988 | Ghajar et al. |
| 4,795,602 A | 1/1989 | Pretchel et al. |
| 4,842,603 A | 6/1989 | Draenert |
| 4,843,112 A | 6/1989 | Gerhart et al. |
| 4,846,814 A | 7/1989 | Ruiz |
| 4,865,586 A | 9/1989 | Hedberg |
| 4,869,906 A | 9/1989 | Dingeldein et al. |
| 4,888,366 A | 12/1989 | Chu et al. |
| 4,900,303 A | 2/1990 | Lemelson |
| 4,961,730 A | 10/1990 | Bodicky et al. |
| 4,961,731 A | 10/1990 | Bodicky |
| 4,963,151 A | 10/1990 | Ducheyene et al. |
| 4,969,870 A | 11/1990 | Kramer et al. |
| 4,969,888 A | 11/1990 | Scholten et al. |
| 4,982,730 A | 1/1991 | Royce |
| 5,059,193 A | 1/1991 | Kuslich |
| 4,998,923 A | 3/1991 | Samson et al. |
| 5,004,501 A | 4/1991 | Faccioli |
| 5,017,627 A | 5/1991 | Bonfield |
| 5,046,513 A | 9/1991 | O'Leary et al. |
| 5,049,137 A | 9/1991 | Thompson |
| 5,049,157 A | 9/1991 | Mittelmeier et al. |
| 5,085,861 A | 2/1992 | Gerhart et al. |
| 5,088,991 A | 2/1992 | Weldon |
| 5,092,891 A | 3/1992 | Kummer et al. |
| 5,103,804 A | 4/1992 | Abele |
| 5,108,404 A | 4/1992 | Scholten et al. |
| 5,112,303 A | 5/1992 | Pudenz et al. |
| 5,114,414 A | 5/1992 | Buchbinder |
| 5,116,305 A | 5/1992 | Milder et al. |
| 5,147,334 A | 9/1992 | Moss |
| 5,156,606 A | 10/1992 | Chin |
| 5,163,431 A | 11/1992 | Greip |
| 5,184,757 A | 2/1993 | Giannuzzi |
| 5,188,619 A | 2/1993 | Myers |
| 5,196,201 A | 3/1993 | Larsson et al. |
| 5,197,971 A | 3/1993 | Bonutti |
| 5,211,631 A | 5/1993 | Sheaff |
| 5,231,989 A | 8/1993 | Middleman et al. |
| 5,242,082 A | 9/1993 | Giannuzzi |
| 5,264,214 A | 11/1993 | Rhee et al. |
| 5,266,248 A | 11/1993 | Ohtsuka et al. |
| 5,269,750 A | 12/1993 | Grulke et al. |
| 5,282,821 A | 2/1994 | Donahue |
| 5,284,128 A | 2/1994 | Hart |
| 5,285,795 A | 2/1994 | Ryan et al. |
| 5,295,980 A | 3/1994 | Ersek |
| 5,296,026 A | 3/1994 | Monroe et al. |
| 5,308,342 A | 5/1994 | Sepetka et al. |
| 5,322,064 A | 6/1994 | Lundquist |
| 5,322,505 A | 6/1994 | Krause et al. |
| 5,334,181 A | 8/1994 | Rubinsky et al. |
| 5,336,699 A | 8/1994 | Cooke et al. |
| 5,343,877 A | 9/1994 | Park |
| 5,352,715 A | 10/1994 | Wallace et al. |
| 5,356,629 A | 10/1994 | Sander |
| 5,360,416 A | 11/1994 | Ausherman et al. |
| 5,368,598 A | 11/1994 | Hasson |
| 5,372,587 A | 12/1994 | Hammerslag et al. |
| 5,378,234 A | 1/1995 | Hammerslag et al. |
| 5,380,307 A | 1/1995 | Chee et al. |
| 5,385,563 A | 1/1995 | Gross |
| 5,389,073 A | 2/1995 | Imran |
| 5,425,770 A | 6/1995 | Piez et al. |
| 5,431,168 A | 7/1995 | Webster, Jr. |
| 5,431,639 A | 7/1995 | Shaw |
| 5,437,636 A | 8/1995 | Snoke et al. |
| 5,449,301 A | 9/1995 | Hanna et al. |
| 5,449,351 A | 9/1995 | Zohmann |
| 5,458,597 A | 10/1995 | Edwards et al. |
| 5,480,382 A | 1/1996 | Hammerslag et al. |
| 5,484,424 A | 1/1996 | Cottenceau et al. |
| 5,489,275 A | 2/1996 | Thompson et al. |
| 5,496,330 A | 3/1996 | Bates et al. |
| 5,512,610 A | 4/1996 | Lin |
| 5,514,130 A | 5/1996 | Baker |
| 5,514,137 A | 5/1996 | Coutts |
| 5,531,715 A | 7/1996 | Engelson et al. |
| 5,535,922 A | 7/1996 | Maziarz |
| 5,549,542 A | 8/1996 | Kovalcheck |
| 5,549,679 A | 8/1996 | Kuslich |
| 5,554,114 A | 9/1996 | Wallace et al. |
| 5,571,085 A | 11/1996 | Accisano, III |
| 5,571,088 A | 11/1996 | Lennox |
| 5,574,075 A | 11/1996 | Draemert |
| 5,599,346 A | 2/1997 | Edwards et al. |
| 5,616,121 A | 4/1997 | McKay |
| 5,620,447 A | 4/1997 | Smith et al. |
| 5,620,467 A | 4/1997 | Wagner |
| 5,624,396 A | 4/1997 | McNamara et al. |
| 5,628,771 A | 5/1997 | Mizukawa et al. |
| 5,637,090 A | 6/1997 | McGee |
| 5,637,091 A | 6/1997 | Hakky et al. |
| 5,662,680 A | 9/1997 | Desai |
| 5,681,282 A | 10/1997 | Eggers et al. |
| 5,681,289 A | 10/1997 | Wilcox et al. |
| 5,681,317 A | 10/1997 | Caldarise |
| 5,685,826 A | 11/1997 | Bonutti |
| 5,695,513 A | 12/1997 | Johnson et al. |
| 5,697,536 A | 12/1997 | Eggers et al. |
| 5,697,909 A | 12/1997 | Eggers et al. |
| 5,700,157 A | 12/1997 | Chung |
| 5,704,926 A | 1/1998 | Sutton |
| 5,709,697 A | 1/1998 | Ratcliff et al. |
| 5,725,568 A | 3/1998 | Hastings |

(56) References Cited

U.S. PATENT DOCUMENTS

| | | |
|---|---|---|
| 5,735,829 A | 4/1998 | Cherian |
| 5,741,320 A | 4/1998 | Thornton et al. |
| 5,766,153 A | 6/1998 | Eggers et al. |
| 5,800,408 A | 9/1998 | Strauss et al. |
| 5,810,804 A | 9/1998 | Gough |
| 5,810,867 A | 9/1998 | Zarbateny et al. |
| 5,820,592 A | 10/1998 | Hammerslag et al. |
| 5,833,632 A | 11/1998 | Jacobsen et al. |
| 5,833,692 A | 11/1998 | Cesarini et al. |
| 5,847,046 A | 12/1998 | Jiang et al. |
| 5,849,028 A | 12/1998 | Chen |
| 5,851,212 A | 12/1998 | Zirps et al. |
| 5,855,577 A | 1/1999 | Murphy-Chutorian et al. |
| 5,858,003 A | 1/1999 | Atala |
| 5,860,952 A | 1/1999 | Quinn |
| 5,860,974 A | 1/1999 | Abele |
| 5,876,373 A | 3/1999 | Giba et al. |
| 5,891,027 A | 4/1999 | Tu |
| 5,902,251 A | 5/1999 | Vanhooydonk |
| 5,902,839 A | 5/1999 | Lautenschlager et al. |
| 5,914,356 A | 6/1999 | Erbe |
| 5,921,956 A | 7/1999 | Grinberg et al. |
| 5,928,239 A | 7/1999 | Mirza |
| 5,931,829 A | 8/1999 | Burbank et al. |
| 5,944,715 A | 8/1999 | Goble et al. |
| 5,947,964 A | 9/1999 | Eggers |
| 5,972,015 A | 10/1999 | Scribner et al. |
| 5,997,581 A | 12/1999 | Khalili |
| 6,019,765 A | 2/2000 | Thornhill et al. |
| 6,027,487 A | 2/2000 | Crocker |
| 6,030,360 A | 2/2000 | Biggs |
| 6,048,346 A | 4/2000 | Reiley et al. |
| 6,059,739 A | 5/2000 | Baumann |
| 6,063,078 A | 5/2000 | Wittkampf |
| 6,064,902 A | 5/2000 | Haissaguerre |
| 6,066,154 A | 5/2000 | Reiley et al. |
| 6,066,176 A | 5/2000 | Oshida |
| 6,073,051 A | 6/2000 | Sharkey et al. |
| 6,080,801 A | 6/2000 | Draenert et al. |
| 6,099,514 A | 8/2000 | Sharkey et al. |
| 6,106,524 A | 8/2000 | Eggers et al. |
| 6,106,539 A | 8/2000 | Fortier |
| 6,110,155 A | 8/2000 | Baudino |
| 6,123,702 A | 9/2000 | Swanson |
| 6,127,597 A | 10/2000 | Beyar et al. |
| 6,135,999 A | 10/2000 | Fanton et al. |
| 6,146,355 A | 11/2000 | Biggs |
| 6,156,254 A | 12/2000 | Andrews et al. |
| 6,183,435 B1 | 2/2001 | Bumbalough et al. |
| 6,203,507 B1 | 3/2001 | Wadsworth et al. |
| 6,203,574 B1 | 3/2001 | Kawamura |
| 6,228,052 B1 | 5/2001 | Pohndorf |
| 6,228,904 B1 | 5/2001 | Yadav et al. |
| 6,231,569 B1 | 5/2001 | Bek et al. |
| 6,231,615 B1 | 5/2001 | Preissman |
| 6,235,043 B1 | 5/2001 | Reiley et al. |
| 6,241,734 B1 | 6/2001 | Scribner et al. |
| 6,248,110 B1 | 6/2001 | Reiley et al. |
| 6,251,092 B1 | 6/2001 | Qin et al. |
| 6,258,086 B1 | 7/2001 | Ashley et al. |
| 6,270,476 B1 | 8/2001 | Santoianni et al. |
| 6,280,413 B1 | 8/2001 | Clark et al. |
| 6,280,434 B1 | 8/2001 | Kinoshita et al. |
| 6,280,441 B1 | 8/2001 | Ryan |
| 6,280,456 B1 | 8/2001 | Scribner et al. |
| 6,280,473 B1 | 8/2001 | Lemperle et al. |
| 6,283,960 B1 | 9/2001 | Ashley |
| 6,291,547 B1 | 9/2001 | Lyles |
| 6,312,428 B1 | 11/2001 | Eggers |
| 6,312,454 B1 | 11/2001 | Stockel et al. |
| 6,332,894 B1 | 12/2001 | Stalcup et al. |
| 6,348,055 B1 | 2/2002 | Preissman |
| 6,352,533 B1 | 3/2002 | Ellman et al. |
| 6,358,251 B1 | 3/2002 | Mirza |
| 6,375,659 B1 | 4/2002 | Erbe et al. |
| 6,383,188 B2 | 5/2002 | Kuslich et al. |
| 6,383,190 B1 | 5/2002 | Preissman |
| 6,395,007 B1 | 5/2002 | Bhatnagar et al. |
| 6,408,889 B1 | 6/2002 | Komachi |
| 6,409,722 B1 | 6/2002 | Hoey et al. |
| 6,428,894 B1 | 6/2002 | Babich et al. |
| 6,437,019 B1 | 8/2002 | Rusin et al. |
| 6,440,138 B1 | 8/2002 | Reiley et al. |
| 6,447,506 B1 | 9/2002 | Swanson et al. |
| 6,447,514 B1 | 9/2002 | Stalcup et al. |
| 6,464,683 B1 | 10/2002 | Samuelson et al. |
| 6,478,793 B1 | 11/2002 | Cosman et al. |
| 6,479,565 B1 | 11/2002 | Stanley |
| 6,484,904 B1 | 11/2002 | Horner et al. |
| 6,506,217 B1 | 1/2003 | Arnett |
| 6,511,471 B2 | 1/2003 | Rosenman et al. |
| 6,524,296 B1 | 2/2003 | Beals |
| 6,565,588 B1 | 5/2003 | Clement et al. |
| 6,575,969 B1 | 6/2003 | Rittman et al. |
| 6,575,978 B2 | 6/2003 | Peterson et al. |
| 6,576,249 B1 | 6/2003 | Gendler et al. |
| 6,582,446 B1 | 6/2003 | Marchosky |
| 6,592,559 B1 * | 7/2003 | Pakter ................ A61B 17/3417 604/272 |
| 6,599,961 B1 | 7/2003 | Pienkowski et al. |
| 6,620,162 B2 | 7/2003 | Kuslich et al. |
| 6,602,248 B1 | 8/2003 | Sharps et al. |
| 6,607,544 B1 | 8/2003 | Boucher et al. |
| 6,613,054 B2 | 9/2003 | Scribner et al. |
| 6,622,731 B2 | 9/2003 | Daniel et al. |
| 6,623,448 B2 | 9/2003 | Slater |
| 6,638,268 B2 | 10/2003 | Niazi |
| 6,663,647 B2 | 10/2003 | Reiley et al. |
| 6,641,587 B2 | 11/2003 | Scribner et al. |
| 6,645,213 B2 | 11/2003 | Sand et al. |
| 6,676,665 B2 | 1/2004 | Foley et al. |
| 6,679,886 B2 | 1/2004 | Weikel et al. |
| 6,689,823 B1 | 2/2004 | Bellare et al. |
| 6,692,532 B1 | 2/2004 | Healy et al. |
| 6,716,216 B1 | 4/2004 | Boucher et al. |
| 6,719,761 B1 | 4/2004 | Reiley et al. |
| 6,719,773 B1 | 4/2004 | Boucher et al. |
| 6,726,691 B2 | 4/2004 | Osorio et al. |
| 6,730,095 B2 | 5/2004 | Olson, Jr. et al. |
| 6,740,090 B1 | 5/2004 | Cragg et al. |
| 6,740,093 B2 | 5/2004 | Hochschuler et al. |
| 6,743,239 B1 | 6/2004 | Kuehn et al. |
| 6,746,451 B2 | 6/2004 | Middleton et al. |
| 6,752,863 B2 | 6/2004 | Lyles et al. |
| 6,753,007 B2 | 6/2004 | Haggard et al. |
| 6,770,079 B2 | 8/2004 | Bhatnagar et al. |
| 6,814,734 B2 | 11/2004 | Chappuis et al. |
| 6,814,736 B2 | 11/2004 | Reiley et al. |
| 6,818,001 B2 | 11/2004 | Wulfman et al. |
| 6,832,984 B2 | 12/2004 | Stelzer et al. |
| 6,835,193 B2 | 12/2004 | Epstein et al. |
| 6,837,867 B2 | 1/2005 | Kortelling |
| 6,863,672 B2 | 3/2005 | Reiley et al. |
| 6,869,430 B2 | 3/2005 | Balbierz et al. |
| 6,869,445 B1 | 3/2005 | Johnson |
| 6,875,219 B2 | 4/2005 | Arramon |
| 6,881,214 B2 | 4/2005 | Cosman et al. |
| 6,887,246 B2 | 5/2005 | Bhatnagar et al. |
| 6,899,715 B1 | 5/2005 | Beaty |
| 6,899,719 B2 | 5/2005 | Reiley et al. |
| 6,907,884 B2 | 6/2005 | Pellegrino et al. |
| 6,913,594 B2 | 7/2005 | Coleman et al. |
| 6,916,306 B1 | 7/2005 | Jenkins et al. |
| 6,923,813 B2 | 8/2005 | Phillips |
| 6,945,956 B2 | 9/2005 | Waldhauser et al. |
| 6,953,594 B2 | 10/2005 | Lee et al. |
| 6,955,716 B2 | 10/2005 | Xu et al. |
| 6,976,987 B2 | 12/2005 | Flores |
| 6,979,312 B2 | 12/2005 | Shimada |
| 6,979,352 B2 | 12/2005 | Reynolds |
| 6,981,981 B2 | 1/2006 | Reiley et al. |
| 6,991,616 B2 | 1/2006 | Bencini et al. |
| 6,998,128 B2 | 2/2006 | Haggard et al. |
| 7,004,930 B2 | 2/2006 | Marshall |

(56) References Cited

U.S. PATENT DOCUMENTS

| | | |
|---|---|---|
| 7,004,945 B2 | 3/2006 | Boyd et al. |
| 7,008,433 B2 | 3/2006 | Voellmicke et al. |
| 7,018,460 B2 | 3/2006 | Xu et al. |
| 7,022,133 B2 | 4/2006 | Yee et al. |
| 7,029,468 B2 | 4/2006 | Honebrink |
| 7,044,954 B2 | 5/2006 | Reiley et al. |
| 7,059,330 B1 | 6/2006 | Makower et al. |
| 7,063,682 B1 | 6/2006 | Whayne et al. |
| 7,066,942 B2 | 6/2006 | Treace |
| RE39,196 E | 7/2006 | Ying et al. |
| 7,081,122 B1 | 7/2006 | Reiley et al. |
| 7,081,161 B2 | 7/2006 | Genge et al. |
| 7,091,258 B2 | 8/2006 | Neubert et al. |
| 7,091,260 B2 | 8/2006 | Kühn |
| 7,094,202 B2 | 8/2006 | Nobis et al. |
| 7,094,286 B2 | 8/2006 | Liu |
| 7,108,696 B2 | 9/2006 | Daniel et al. |
| 7,109,254 B2 | 9/2006 | Müller et al. |
| 7,112,205 B2 | 9/2006 | Carrison |
| 7,114,501 B2 | 10/2006 | Johnson et al. |
| 7,138,442 B2 | 11/2006 | Smith et al. |
| 7,153,306 B2 | 12/2006 | Ralph et al. |
| 7,153,307 B2 | 12/2006 | Scribner et al. |
| 7,156,843 B2 | 1/2007 | Skarda |
| 7,156,845 B2 | 1/2007 | Mulier |
| 7,172,629 B2 | 2/2007 | McKay et al. |
| 7,179,255 B2 | 2/2007 | Lettice et al. |
| 7,186,234 B2 | 3/2007 | Dahla et al. |
| 7,186,761 B2 | 3/2007 | Soffiati et al. |
| 7,226,481 B2 | 6/2007 | Kuslich et al. |
| 7,252,671 B2 | 8/2007 | Scribner et al. |
| 7,267,683 B2 | 9/2007 | Sharkey et al. |
| 7,270,661 B2 | 9/2007 | Dahla et al. |
| 7,294,127 B2 | 11/2007 | Leung |
| 7,465,318 B2 | 12/2008 | Sennett et al. |
| 7,480,533 B2 | 1/2009 | Cosman et al. |
| 7,503,920 B2 | 3/2009 | Siegal |
| 7,544,196 B2 | 6/2009 | Bagga et al. |
| 7,559,932 B2 | 7/2009 | Truckai et al. |
| 7,569,054 B2 | 8/2009 | Michelson |
| 7,572,263 B2 | 8/2009 | Preissman |
| 7,591,822 B2 | 9/2009 | Olson, Jr. et al. |
| 7,625,364 B2 | 12/2009 | Corcoran et al. |
| 7,641,664 B2 | 1/2010 | Pagano |
| 7,731,720 B2 | 6/2010 | Sand et al. |
| 7,811,291 B2 | 10/2010 | Liu et al. |
| 7,824,403 B2 | 11/2010 | Vaska |
| 7,842,041 B2 | 11/2010 | Liu et al. |
| 7,887,543 B2 | 2/2011 | Sand et al. |
| 7,905,884 B2 | 3/2011 | Simonton et al. |
| 7,918,874 B2 | 4/2011 | Siegal |
| 7,972,340 B2 | 7/2011 | Sand et al. |
| 7,976,542 B1 | 7/2011 | Cosman |
| 8,034,071 B2 | 10/2011 | Scribner et al. |
| 8,246,627 B2 | 8/2012 | Vanleeuwen et al. |
| 8,284,128 B2 | 10/2012 | Kimura |
| 8,518,036 B2 | 8/2013 | Leung |
| 8,583,260 B2 | 11/2013 | Knudson |
| 8,591,507 B2 | 11/2013 | Kramer et al. |
| 8,663,226 B2 | 3/2014 | Germain |
| RE44,883 E | 5/2014 | Cha |
| 8,758,349 B2 | 6/2014 | Germain et al. |
| 8,827,981 B2 | 9/2014 | Liu et al. |
| 8,864,760 B2 | 10/2014 | Kramer et al. |
| 8,936,631 B2 | 1/2015 | Nguyen |
| 9,113,974 B2 | 8/2015 | Germain |
| 9,125,671 B2 | 9/2015 | Germain et al. |
| 9,161,809 B2 | 10/2015 | Germain et al. |
| 9,421,057 B2 | 8/2016 | Germain |
| 9,743,938 B2 | 8/2017 | Germain et al. |
| 2001/0011174 A1 | 8/2001 | Reiley et al. |
| 2001/0023349 A1 | 9/2001 | Van Tassel et al. |
| 2002/0007180 A1 | 1/2002 | Wittenberger et al. |
| 2002/0013600 A1 | 1/2002 | Scribner et al. |
| 2002/0026195 A1 | 2/2002 | Layne et al. |
| 2002/0026197 A1 | 2/2002 | Foley et al. |
| 2002/0068929 A1 | 6/2002 | Zvuloni |
| 2002/0068974 A1 | 6/2002 | Kuslich et al. |
| 2002/0077595 A1 | 6/2002 | Hundertmark et al. |
| 2002/0082605 A1 | 6/2002 | Reiley et al. |
| 2002/0115742 A1 | 8/2002 | Trieu et al. |
| 2002/0128638 A1 | 9/2002 | Chauvet et al. |
| 2002/0133148 A1 | 9/2002 | Daniel et al. |
| 2002/0156483 A1 | 10/2002 | Voellmicke et al. |
| 2002/0188299 A1 | 12/2002 | Reiley et al. |
| 2002/0188300 A1 | 12/2002 | Arramon et al. |
| 2003/0014094 A1 | 1/2003 | Hammack et al. |
| 2003/0032929 A1 | 2/2003 | McGuckin |
| 2003/0036763 A1 | 2/2003 | Bhatnagar et al. |
| 2003/0043963 A1 | 3/2003 | Yamagami et al. |
| 2003/0050644 A1 | 3/2003 | Boucher et al. |
| 2003/0069522 A1 | 4/2003 | Jasobsen et al. |
| 2003/0073979 A1 | 4/2003 | Naimark et al. |
| 2003/0130664 A1 | 7/2003 | Boucher et al. |
| 2003/0163085 A1 | 8/2003 | Tanner et al. |
| 2003/0171744 A1 | 9/2003 | Leung et al. |
| 2003/0191489 A1 | 10/2003 | Reiley et al. |
| 2003/0195547 A1 | 10/2003 | Scribner et al. |
| 2003/0212394 A1 | 11/2003 | Pearson et al. |
| 2003/0212395 A1 | 11/2003 | Woloszko et al. |
| 2003/0220414 A1 | 11/2003 | Axen et al. |
| 2003/0225432 A1 | 12/2003 | Baptiste et al. |
| 2003/0233096 A1 | 12/2003 | Osorio et al. |
| 2004/0023384 A1 | 2/2004 | Fukaya |
| 2004/0023784 A1 | 2/2004 | Yu et al. |
| 2004/0024081 A1 | 2/2004 | Trieu et al. |
| 2004/0024398 A1 | 2/2004 | Hovda et al. |
| 2004/0024409 A1 | 2/2004 | Sand et al. |
| 2004/0024410 A1 | 2/2004 | Olson et al. |
| 2004/0034384 A1 | 2/2004 | Fukaya |
| 2004/0044096 A1 | 3/2004 | Smith et al. |
| 2004/0044350 A1 | 3/2004 | Martin et al. |
| 2004/0059328 A1 | 3/2004 | Daniel et al. |
| 2004/0087936 A1 | 5/2004 | Stern et al. |
| 2004/0087994 A1 | 5/2004 | Suddaby |
| 2004/0092946 A1 | 5/2004 | Bagga et al. |
| 2004/0097612 A1 | 5/2004 | Rosenberg et al. |
| 2004/0111136 A1 | 6/2004 | Sharkey et al. |
| 2004/0127987 A1 | 7/2004 | Evans et al. |
| 2004/0133208 A1 | 7/2004 | Weikel et al. |
| 2004/0138758 A1 | 7/2004 | Evans et al. |
| 2004/0153064 A1 | 8/2004 | Foley et al. |
| 2004/0153115 A1 | 8/2004 | Reiley et al. |
| 2004/0158237 A1 | 8/2004 | Abboud et al. |
| 2004/0167561 A1 | 8/2004 | Boucher et al. |
| 2004/0167562 A1 | 8/2004 | Osorio et al. |
| 2004/0167625 A1 | 8/2004 | Beyar et al. |
| 2004/0210231 A1 | 10/2004 | Boucher et al. |
| 2004/0215343 A1 | 10/2004 | Hochschuler et al. |
| 2004/0220577 A1 | 11/2004 | Cragg |
| 2004/0220680 A1 | 11/2004 | Yamamoto et al. |
| 2004/0225296 A1 | 11/2004 | Reiss et al. |
| 2004/0226479 A1 | 11/2004 | Lyles et al. |
| 2004/0230309 A1 | 11/2004 | DiMauro et al. |
| 2004/0236186 A1 | 11/2004 | Chu |
| 2004/0247644 A1 | 12/2004 | Bratt et al. |
| 2004/0267271 A9 | 12/2004 | Scribner et al. |
| 2005/0027245 A1 | 2/2005 | Sachdeva et al. |
| 2005/0033303 A1 | 2/2005 | Chappuis et al. |
| 2005/0038383 A1 | 2/2005 | Kelley et al. |
| 2005/0038422 A1 | 2/2005 | Maurice |
| 2005/0043737 A1 | 2/2005 | Reiley et al. |
| 2005/0055030 A1 | 3/2005 | Falahee |
| 2005/0060030 A1 | 3/2005 | Lashinski et al. |
| 2005/0070844 A1 | 3/2005 | Chow et al. |
| 2005/0070912 A1 | 3/2005 | Voellmicke |
| 2005/0070915 A1 | 3/2005 | Mazzuca et al. |
| 2005/0090852 A1 | 4/2005 | Layne et al. |
| 2005/0113836 A1 | 5/2005 | Lozier et al. |
| 2005/0119650 A1 | 6/2005 | Sanders et al. |
| 2005/0124989 A1 | 6/2005 | Suddaby |
| 2005/0143827 A1 | 6/2005 | Globerman et al. |
| 2005/0177168 A1 | 8/2005 | Brunnett et al. |
| 2005/0177210 A1 | 8/2005 | Leung et al. |

(56) References Cited

U.S. PATENT DOCUMENTS

| | | |
|---|---|---|
| 2005/0182412 A1 | 8/2005 | Johnson et al. |
| 2005/0182413 A1 | 8/2005 | Johnson et al. |
| 2005/0187556 A1 | 8/2005 | Stack et al. |
| 2005/0199156 A1 | 9/2005 | Khairoun et al. |
| 2005/0209557 A1 | 9/2005 | Carroll et al. |
| 2005/0216018 A1 | 9/2005 | Sennett |
| 2005/0228391 A1 | 10/2005 | Levy et al. |
| 2005/0234425 A1 | 10/2005 | Miller et al. |
| 2005/0240193 A1 | 10/2005 | Layne et al. |
| 2005/0251266 A1 | 11/2005 | Maspero et al. |
| 2005/0251267 A1 | 11/2005 | Winterbottom et al. |
| 2005/0261683 A1 | 11/2005 | Veldhuizen et al. |
| 2005/0283148 A1 | 12/2005 | Janssen |
| 2005/0287771 A1 | 12/2005 | Seamons et al. |
| 2006/0024348 A1 | 2/2006 | Engqvist et al. |
| 2006/0025763 A1 | 2/2006 | Nelson et al. |
| 2006/0041033 A1 | 2/2006 | Bisig et al. |
| 2006/0052743 A1 | 3/2006 | Reynolds |
| 2006/0064101 A1 | 3/2006 | Arramon |
| 2006/0074433 A1 | 4/2006 | McGill et al. |
| 2006/0084977 A1 | 4/2006 | Lieberman |
| 2006/0085009 A1 | 4/2006 | Truckai et al. |
| 2006/0100635 A1 | 5/2006 | Reiley et al. |
| 2006/0100706 A1 | 5/2006 | Shadduck et al. |
| 2006/0106392 A1 | 5/2006 | Embry |
| 2006/0106459 A1 | 5/2006 | Truckai et al. |
| 2006/0116689 A1 | 6/2006 | Albans et al. |
| 2006/0116690 A1 | 6/2006 | Pagano |
| 2006/0122623 A1 | 6/2006 | Truckai et al. |
| 2006/0142732 A1 | 6/2006 | Karmarkar et al. |
| 2006/0149268 A1 | 7/2006 | Truckai et al. |
| 2006/0149281 A1 | 7/2006 | Reiley et al. |
| 2006/0156959 A1 | 7/2006 | Engqvist et al. |
| 2006/0184106 A1 | 8/2006 | McDaniel et al. |
| 2006/0184192 A1 | 8/2006 | Markworth et al. |
| 2006/0200121 A1 | 9/2006 | Mowery |
| 2006/0206116 A1 | 9/2006 | Yeung |
| 2006/0206136 A1 | 9/2006 | Sachdeva et al. |
| 2006/0217704 A1 | 9/2006 | Cockburn et al. |
| 2006/0217736 A1 | 9/2006 | Kaneko |
| 2006/0229625 A1 | 10/2006 | Truckai et al. |
| 2006/0229631 A1 | 10/2006 | Reiley et al. |
| 2006/0235417 A1 | 10/2006 | Sala |
| 2006/0259023 A1 | 11/2006 | Abboud et al. |
| 2006/0264819 A1 | 11/2006 | Fischer et al. |
| 2006/0264945 A1 | 11/2006 | Edidin et al. |
| 2006/0266372 A1 | 11/2006 | Miller et al. |
| 2006/0270750 A1 | 11/2006 | Almen et al. |
| 2006/0271061 A1 | 11/2006 | Beyar et al. |
| 2006/0276797 A1 | 12/2006 | Botimer |
| 2006/0276819 A1 | 12/2006 | Osorio et al. |
| 2006/0293687 A1 | 12/2006 | Bogert |
| 2007/0006692 A1 | 1/2007 | Phan |
| 2007/0010845 A1 | 1/2007 | Gong et al. |
| 2007/0016130 A1 | 1/2007 | Leeflang et al. |
| 2007/0016211 A1 | 1/2007 | Botimer |
| 2007/0021769 A1 | 1/2007 | Scribner et al. |
| 2007/0043373 A1 | 2/2007 | Sala |
| 2007/0055201 A1 | 3/2007 | Seto et al. |
| 2007/0055260 A1 | 3/2007 | Cragg |
| 2007/0055266 A1 | 3/2007 | Osorio et al. |
| 2007/0055275 A1 | 3/2007 | Schaller |
| 2007/0055277 A1 | 3/2007 | Osorio et al. |
| 2007/0055278 A1 | 3/2007 | Osorio et al. |
| 2007/0055279 A1 | 3/2007 | Sand et al. |
| 2007/0055281 A1 | 3/2007 | Osorio et al. |
| 2007/0055283 A1 | 3/2007 | Scribner |
| 2007/0055284 A1 | 3/2007 | Osorio |
| 2007/0055285 A1 | 3/2007 | Osorio et al. |
| 2007/0055300 A1 | 3/2007 | Osorio et al. |
| 2007/0055382 A1 | 3/2007 | Osorio et al. |
| 2007/0059281 A1 | 3/2007 | Moseley et al. |
| 2007/0067034 A1 | 3/2007 | Chirico et al. |
| 2007/0093840 A1 | 4/2007 | Pacelli |
| 2007/0114248 A1 | 5/2007 | Kovac |
| 2007/0118142 A1 | 5/2007 | Krueger et al. |
| 2007/0118143 A1 | 5/2007 | Ralph et al. |
| 2007/0142842 A1 | 6/2007 | Krueger et al. |
| 2007/0156130 A1 | 7/2007 | Thistle |
| 2007/0162042 A1 | 7/2007 | Dunker |
| 2007/0173939 A1 | 7/2007 | Kim et al. |
| 2007/0185231 A1 | 8/2007 | Liu et al. |
| 2007/0197935 A1 | 8/2007 | Reiley |
| 2007/0198023 A1 | 8/2007 | Sand et al. |
| 2007/0211563 A1 | 9/2007 | Devries |
| 2007/0233146 A1 | 10/2007 | Henniges et al. |
| 2007/0260223 A1 | 11/2007 | Scheibe et al. |
| 2007/0260257 A1 | 11/2007 | Phan |
| 2007/0270876 A1 | 11/2007 | Kuo et al. |
| 2007/0276319 A1 | 11/2007 | Betts |
| 2007/0282305 A1 | 12/2007 | Goldfarb et al. |
| 2008/0004615 A1 | 1/2008 | Woloszko et al. |
| 2008/0033422 A1 | 2/2008 | Turner et al. |
| 2008/0058725 A1 | 3/2008 | Scribner et al. |
| 2008/0058821 A1 | 3/2008 | Maurer et al. |
| 2008/0058827 A1 | 3/2008 | Osorio et al. |
| 2008/0058840 A1 | 3/2008 | Albrecht |
| 2008/0065020 A1 | 3/2008 | Ralph et al. |
| 2008/0065087 A1 | 3/2008 | Osorio et al. |
| 2008/0065190 A1 | 3/2008 | Osorio et al. |
| 2008/0086142 A1 | 4/2008 | Kohm et al. |
| 2008/0140079 A1 | 6/2008 | Osorio et al. |
| 2008/0183165 A1 | 7/2008 | Buysse et al. |
| 2008/0183265 A1 | 7/2008 | Bly |
| 2008/0195112 A1 | 8/2008 | Liu et al. |
| 2008/0208255 A1 | 8/2008 | Siegal |
| 2008/0221608 A1 | 9/2008 | Betts |
| 2008/0228192 A1 | 9/2008 | Beyer et al. |
| 2008/0249481 A1 | 10/2008 | Crainich |
| 2008/0249525 A1 | 10/2008 | Lee et al. |
| 2008/0255571 A1 | 10/2008 | Truckai et al. |
| 2008/0269766 A1 | 10/2008 | Justis |
| 2008/0269796 A1 | 10/2008 | Reiley et al. |
| 2008/0287741 A1 | 11/2008 | Ostrovsky et al. |
| 2008/0294167 A1 | 11/2008 | Schumacher et al. |
| 2009/0076517 A1 | 3/2009 | Reiley et al. |
| 2009/0105775 A1 | 4/2009 | Mitchell et al. |
| 2009/0131867 A1 | 5/2009 | Liu et al. |
| 2009/0131886 A1 | 5/2009 | Liu et al. |
| 2009/0131945 A1 | 5/2009 | Liu et al. |
| 2009/0131948 A1 | 5/2009 | Liu |
| 2009/0131950 A1 | 5/2009 | Liu et al. |
| 2009/0131986 A1 | 5/2009 | Lee |
| 2009/0182427 A1 | 7/2009 | Liu et al. |
| 2009/0198243 A1 | 8/2009 | Melsheimer |
| 2009/0264862 A1 | 10/2009 | Neidert et al. |
| 2009/0264892 A1 | 10/2009 | Beyar et al. |
| 2009/0292289 A9 | 11/2009 | Sand et al. |
| 2009/0293687 A1 | 12/2009 | Nino et al. |
| 2009/0299282 A1 | 12/2009 | Lau et al. |
| 2010/0057087 A1 | 3/2010 | Cha |
| 2010/0082033 A1 | 4/2010 | Germain |
| 2010/0114184 A1 | 5/2010 | Degtyar |
| 2010/0121332 A1 | 5/2010 | Crainich et al. |
| 2010/0152724 A1 | 6/2010 | Marion et al. |
| 2010/0160922 A1 | 6/2010 | Liu et al. |
| 2010/0211076 A1 | 8/2010 | Germain et al. |
| 2010/0274270 A1 | 10/2010 | Patel |
| 2010/0298832 A1 | 11/2010 | Lau et al. |
| 2011/0034884 A9 | 2/2011 | Pellegrino et al. |
| 2011/0098701 A1 | 4/2011 | Mcintyre et al. |
| 2011/0160737 A1 | 6/2011 | Steffen et al. |
| 2011/0251615 A1 | 10/2011 | Truckai et al. |
| 2011/0295261 A1 | 12/2011 | Germain |
| 2011/0295262 A1 | 12/2011 | Germain et al. |
| 2011/0301590 A1 | 12/2011 | Podhajsky et al. |
| 2012/0065543 A1 | 3/2012 | Ireland |
| 2012/0130381 A1 | 5/2012 | Germain |
| 2012/0158004 A1 | 6/2012 | Burger et al. |
| 2012/0191095 A1 | 7/2012 | Burger et al. |
| 2012/0239049 A1 | 9/2012 | Truckai |
| 2012/0265186 A1 | 10/2012 | Burger et al. |
| 2012/0277730 A1 | 11/2012 | Salahieh |
| 2012/0330180 A1 | 12/2012 | Pellegrino et al. |

(56) References Cited

U.S. PATENT DOCUMENTS

| | | | |
|---|---|---|---|
| 2012/0330301 | A1 | 12/2012 | Pellegrino et al. |
| 2013/0006232 | A1 | 1/2013 | Pellegrino |
| 2013/0041377 | A1 | 2/2013 | Kuntz |
| 2013/0072941 | A1 | 3/2013 | Tan-Malecki et al. |
| 2013/0231654 | A1 | 9/2013 | Germain |
| 2013/0237795 | A1 | 9/2013 | Carr |
| 2013/0261615 | A1 | 10/2013 | Kramer et al. |
| 2013/0261621 | A1 | 10/2013 | Kramer et al. |
| 2013/0345709 | A1 | 12/2013 | Burger et al. |
| 2014/0135779 | A1 | 5/2014 | Germain |
| 2014/0163566 | A1 | 6/2014 | Phan et al. |
| 2014/0316413 | A1 | 10/2014 | Burger et al. |
| 2014/0350542 | A1 | 11/2014 | Kramer et al. |
| 2014/0371740 | A1 | 12/2014 | Germain et al. |
| 2015/0216594 | A1 | 8/2015 | Prakash |
| 2015/0297246 | A1 | 10/2015 | Patel et al. |
| 2015/0313614 | A1 | 11/2015 | Germain |
| 2016/0228131 | A1 | 6/2016 | Brockman et al. |

FOREIGN PATENT DOCUMENTS

| | | |
|---|---|---|
| CN | 2841051 | 11/2006 |
| JP | 2004242936 | 9/2004 |
| JP | 2008510530 | 4/2008 |
| JP | 2008528081 | 7/2008 |
| JP | 2008541878 | 11/2008 |
| JP | 2010063887 | 3/2010 |
| JP | 2011500156 | 1/2011 |
| WO | 1993004634 | 3/1993 |
| WO | 1996013297 | 5/1996 |
| WO | 1996020752 | 7/1996 |
| WO | 199703611 | 2/1997 |
| WO | 1997003611 | 2/1997 |
| WO | 2002003870 | 1/2002 |
| WO | 2003101308 | 12/2003 |
| WO | 2005122938 | 12/2005 |
| WO | 2007036815 | 4/2007 |
| WO | 2007087400 | 8/2007 |
| WO | 2008076330 | 6/2008 |
| WO | 2008084479 | 7/2008 |
| WO | 2010039894 | 4/2010 |
| WO | 2010081187 | 7/2010 |
| WO | 2010135602 | 11/2010 |
| WO | 2010135606 | 11/2010 |
| WO | 2011066465 | 6/2011 |
| WO | 2011114602 | 9/2011 |
| WO | 2011137357 | 11/2011 |
| WO | 2011137377 | 11/2011 |
| WO | 2012071464 | 5/2012 |
| WO | 2013147990 | 10/2013 |
| WO | 2014093673 | 6/2014 |

OTHER PUBLICATIONS

Office Action dated Jan. 18, 2017 for U.S. Appl. No. 14/815,620.
Office Action dated May 17, 2010 for U.S. Appl. No. 12/261,987.
Office Action dated May 21, 2014 for U.S. Appl. No. 13/098,116.
Office Action dated May 24, 2012 for U.S. Appl. No. 12/578,455.
Office Action dated May 31, 2016 for U.S. Appl. No. 14/815,620.
Office Action dated Jun. 4, 2018 for U.S. Appl. No. 15/349,715.
Office Action dated Jun. 8, 2009 for U.S. Appl. No. 11/941,764.
Office Action dated Jun. 12, 2009 for U.S. Appl. No. 11/941,733.
Office Action dated Jun. 21, 2013 for U.S. Appl. No. 13/215,098.
Office Action dated Jun. 22, 2018 for U.S. Appl. No. 15/917,454.
Office Action dated Jun. 25, 2015 for U.S. Appl. No. 13/853,397.
Office Action dated Jun. 29, 2018 for U.S. Appl. No. 15/449,591.
Office Action dated Jul. 11, 2017 for U.S. Appl. No. 14/815,812.
Office Action dated Jul. 12, 2010 for U.S. Appl. No. 11/941,764.
Office Action dated Jul. 12, 2017 for U.S. Appl. No. 13/083,411.
Office Action dated Jul. 25, 2011 for U.S. Appl. No. 11/941,733.
Office Action dated Jul. 29, 2013 for U.S. Appl. No. 13/098,116.
Office Action dated Jul. 30, 2013 for U.S. Appl. No. 13/083,411.
Office Action dated Sep. 1, 2010 for U.S. Appl. No. 12/029,428.
Office Action dated Sep. 6, 2017 for U.S. Appl. No. 15/211,359.
Office Action dated Sep. 26, 2017 for U.S. Appl. No. 15/388,598.
Office Action dated Oct. 2, 2018 for U.S. Appl. No. 14/139,372.
Office Action dated Oct. 30, 2018 for U.S. Appl. No. 15/349,715.
Office Action dated Nov. 3, 2008 for U.S. Appl. No. 11/941,764.
Office Action dated Nov. 3, 2008 for U.S. Appl. No. 12/029,428.
Office Action dated Nov. 5, 2008 for U.S. Appl. No. 11/941,733.
Office Action dated Nov. 12, 2013 for U.S. Appl. No. 13/083,411.
Office Action dated Nov. 25, 2016 for U.S. Appl. No. 13/083,411.
Office Action dated Dec. 2, 2009 for U.S. Appl. No. 12/029,428.
Office Action dated Dec. 3, 2012 for U.S. Appl. No. 12/571,174.
Office Action dated Dec. 9, 2009 for U.S. Appl. No. 12/262,064.
Office Action dated Dec. 11, 2009 for U.S. Appl. No. 12/261,987.
Office Action dated Feb. 27, 2013 for U.S. Appl. No. 12/578,455.
Office Action dated Jul. 12, 2016 for U.S. Appl. No. 14/887,007.
Office Action dated Sep. 10, 2013 for U.S. Appl. No. 12/571,174.
Disc-O-Tech confidence Cement System at http://www.disc-o-tech.com/Articles/Article.asp?CategoryID=4&ArticleID=168 accessed, Dec. 3, 2007.
Dai, et al., Bone-Particle-Impregnated Bone Cement: an in vivo weight-bearing study, Journal Biomedical Materials Search, vol. 25, 191 ,141-156.
Hasenwinkel, et al.,"A Novel High-Viscosity, Two-Solution Acrylic Bone Cement: Effect of Chemical Composition on Properties", J. Biomed Mater. Res. vol. 47, No. 1 ,1999 ,36-45.
Klawitter, et al., Application of Porous Ceramics for the Attachment of Load Bearing Internal Orthopedic Applications, J. Biomed. Mater. Res. Symp., 2(1) ,1972 ,61-229.
Liu, et al., Bone-Particle-Impregnanted Bone Cement: An In Vitro Study, Journal of Biomedical Materials Research, vol. 21 ,1987, 247-261.
Park, et al., Biomaterials: An Introduction—Second Edition, Plenum Press ,1992 ,177-178.
Park, et al., The Materials Properties of Bone-Particle Impregnated PMMA, Journal of Biomedical Engineering, vol. 108 ,1986 ,141-148.
International Search Report and Written Opinion dated Mar. 30, 2018 for PCT/US2017/065328.
U.S. Appl. No. 15/836,241, filed Dec. 8, 2017.
European Examination Report dated Dec. 19, 2017 for EP13767383.6.
European Search Report dated Jan. 7, 2019 for EP16793433.0.
European Search Report dated Jun. 8, 2017 for EP17154660.9.
European Search Report dated Nov. 15, 2017 for EP09818476.5.
European Search Report dated Nov. 16, 2016 for EP14772615.2.
International Search Report and Written Opinion dated Jan. 9, 2012 for PCT/US2011/034185.
International Search Report and Written Opinion dated Jan. 22, 2009 for PCT/US2008/83698.
International Search Report and Written Opinion dated Feb. 7, 2018 for PCT/US2017/058303.
International Search Report and Written Opinion dated Feb. 21, 2018 for PCT/US2017/063281.
International Search Report and Written Opinion dated Apr. 23, 2016 for PCT/US2018/012372.
International Search Report and Written Opinion dated Jul. 20, 2010 for PCT/US2010/035687.
International Search Report and Written Opinion dated Jul. 26, 2011 for PCT/US2011/034628.
International Search Report and Written Opinion dated Aug. 25, 2009 for PCT/US2009/035726.
International Search Report and Written Opinion dated Nov. 20, 2009 for PCT/US2009/059113.
Notice of Allowance dated Jan. 4, 2017 for U.S. Appl. No. 13/302,927.
Notice of Allowance dated Jan. 18, 2017 for U.S. Appl. No. 13/097,998.
Notice of Allowance dated Feb. 21, 2019 for U.S. Appl. No. 14/139,372.
Notice of Allowance dated Apr. 3, 2019 for U.S. Appl. No. 15/349,715.
Notice of Allowance dated Apr. 9, 2014 for U.S. Appl. No. 12/578,455.
Notice of Allowance dated Apr. 23, 2018 for U.S. Appl. No. 13/083,411.

(56) References Cited

OTHER PUBLICATIONS

Notice of Allowance dated May 3, 2017 for U.S. Appl. No. 14/815,620.
Notice of Allowance dated May 11, 2018 for U.S. Appl. No. 14/453,427.
Notice of Allowance dated May 26, 2015 for U.S. Appl. No. 13/098,116.
Notice of Allowance dated Aug. 24, 2018 for U.S. Appl. No. 15/388,598.
Notice of Allowance dated Oct. 28, 2016 for U.S. Appl. No. 13/853,397.
Notice of Allowance dated Nov. 8, 2013 for U.S. Appl. No. 12/578,455.
Notice of Allowance dated Nov. 9, 2017 for U.S. Appl. No. 14/815,812.
Notice of Allowance dated Nov. 18, 2016 for U.S. Appl. No. 13/097,998.
Notice of Allowance dated Nov. 25, 2013 for U.S. Appl. No. 12/571,174.
Notice of Allowance dated Nov. 25, 2018 for U.S. Appl. No. 13/853,397.
Notice of Allowance dated Dec. 13, 2018 for U.S. Appl. No. 15/917,454.
Notice of Allowance dated Dec. 28, 2017 for U.S. Appl. No. 15/211,359.
Notice of Allowance dated Aug. 31, 2016 for U.S. Appl. No. 14/887,007.
Office Action dated Jan. 26, 2011 for U.S. Appl. No. 11/941,764.
Office Action dated Jan. 26, 2017 for U.S. Appl. No. 14/815,812.
Office Action dated Feb. 3, 2016 for U.S. Appl. No. 13/853,397.
Office Action dated Feb. 10, 2015 for U.S. Appl. No. 13/083,411.
Office Action dated Feb. 23, 2010 for U.S. Appl. No. 11/941,733.
Office Action dated Feb. 23, 2010 for U.S. Appl. No. 11/941,764.
Office Action dated Mar. 1, 2017 for U.S. Appl. No. 15/211,359.
Office Action dated Mar. 21, 2011 for U.S. Appl. No. 11/941,764.
Office Action dated Mar. 21, 2011 for U.S. Appl. No. 12/029,428.
Office Action dated Apr. 19, 2018 for U.S. Appl. No. 15/388,598.
Office Action dated Apr. 24, 2017 for U.S. Appl. No. 14/453,427.
Office Action dated Apr. 26, 2010 for U.S. Appl. No. 12/029,428.
Office Action dated May 1, 2009 for U.S. Appl. No. 12/261,987.
Office Action dated May 5, 2010 for U.S. Appl. No. 11/941,764.
Office Action dated May 6, 2019 for U.S. Appl. No. 15/675,315.
Office Action dated May 13, 2009 for U.S. Appl. No. 12/029,428.

* cited by examiner

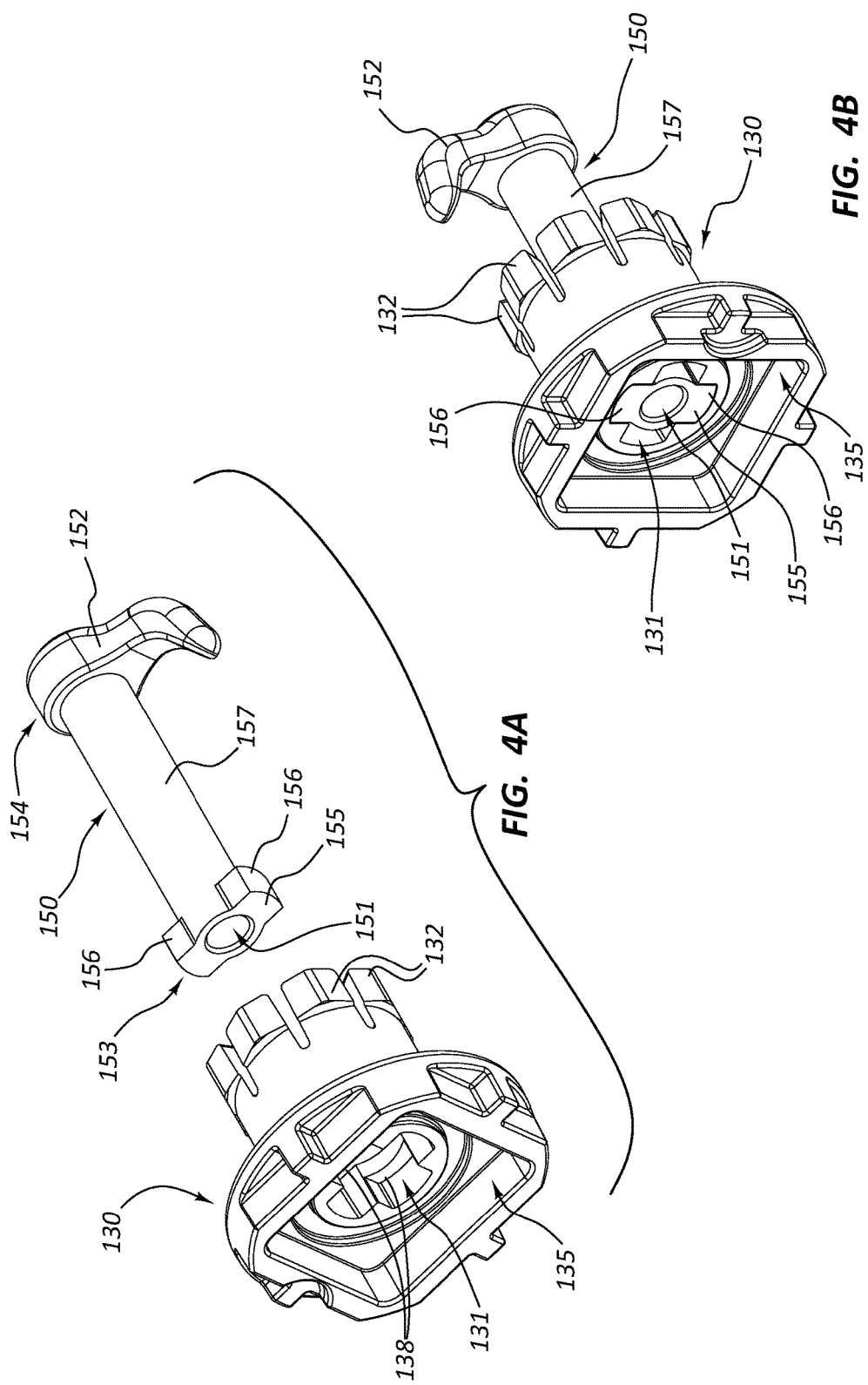

FIG. 5A1
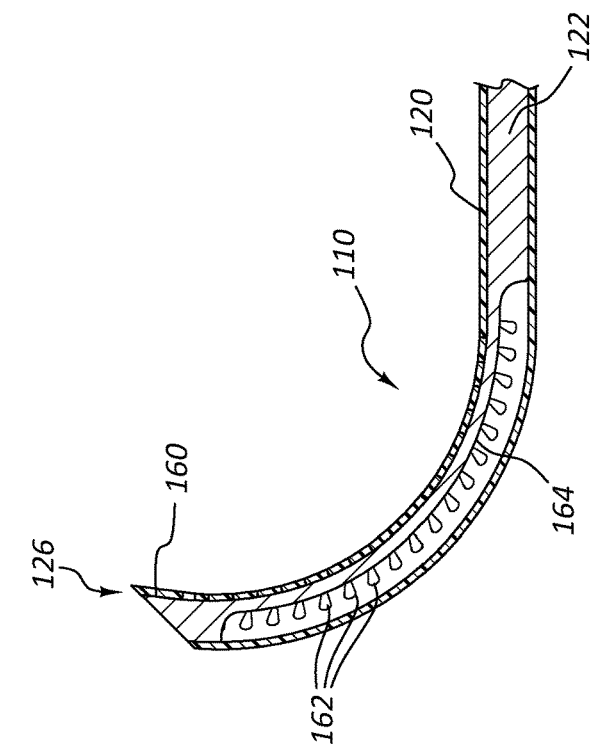
FIG. 5A2
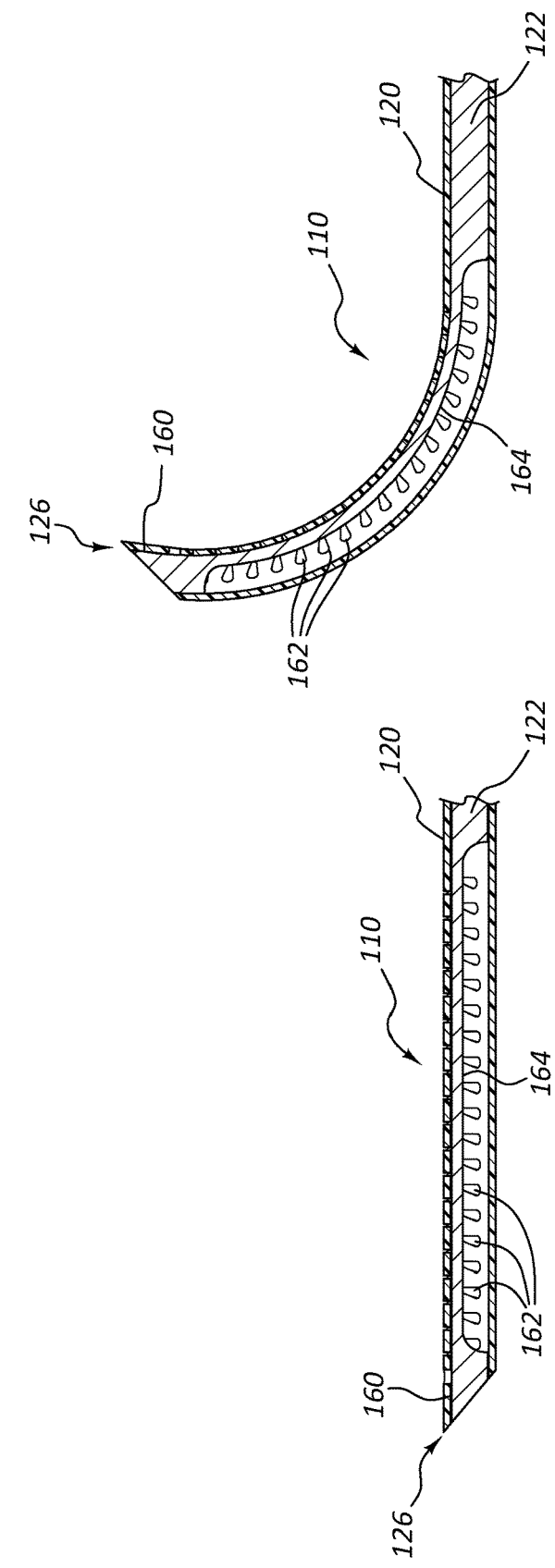
FIG. 5B
FIG. 5C

MEDICAL DEVICES FOR TREATING HARD TISSUES AND RELATED METHODS

RELATED APPLICATIONS

This application claims priority to U.S. Provisional Application No. 62/432,182, filed on Dec. 9, 2016 and titled, "Medical Devices for Treating Hard Tissues and Related Methods," and U.S. Provisional Application No. 62/432,217, filed on Dec. 9, 2016 and titled, "Medical Devices for Treating Hard Tissues and Related Methods," both of which are hereby incorporated by reference in their entireties.

TECHNICAL FIELD

The present disclosure relates generally to the field of medical devices. More specifically, the medical devices may include osteotomes. The medical devices may include deflectable working end portions. The medical devices may also include indicators for communicating a direction of deflection of a working end portion. Related methods are also disclosed.

BRIEF DESCRIPTION OF THE DRAWINGS

The embodiments disclosed herein will become more fully apparent from the following description and appended claims, taken in conjunction with the accompanying drawings. While various aspects of the embodiments are presented in drawings, the drawings depict only typical embodiments, which will be described with additional specificity and detail through use of the accompanying drawings in which:

FIG. 4A is a perspective view of an indicator and a distal collar of the medical device of FIG. 1 in an uncoupled configuration.

FIG. 4B is a perspective view of the indicator and the distal collar of FIG. 4A in a coupled configuration.

FIG. 5A1 is a cross-sectional view of the inner member of FIG. 5A through line 5A1-5A1.

FIG. 5A2 is a cross-sectional view of the inner member of FIG. 5A through line 5A2-5A2.

FIG. 5B is a cross-sectional view of a working end portion of the medical device of FIG. 1 in an undeflected configuration.

FIG. 5C is a cross-sectional view of the working end portion of FIG. 5B in a deflected configuration.

DETAILED DESCRIPTION

Figure 1:
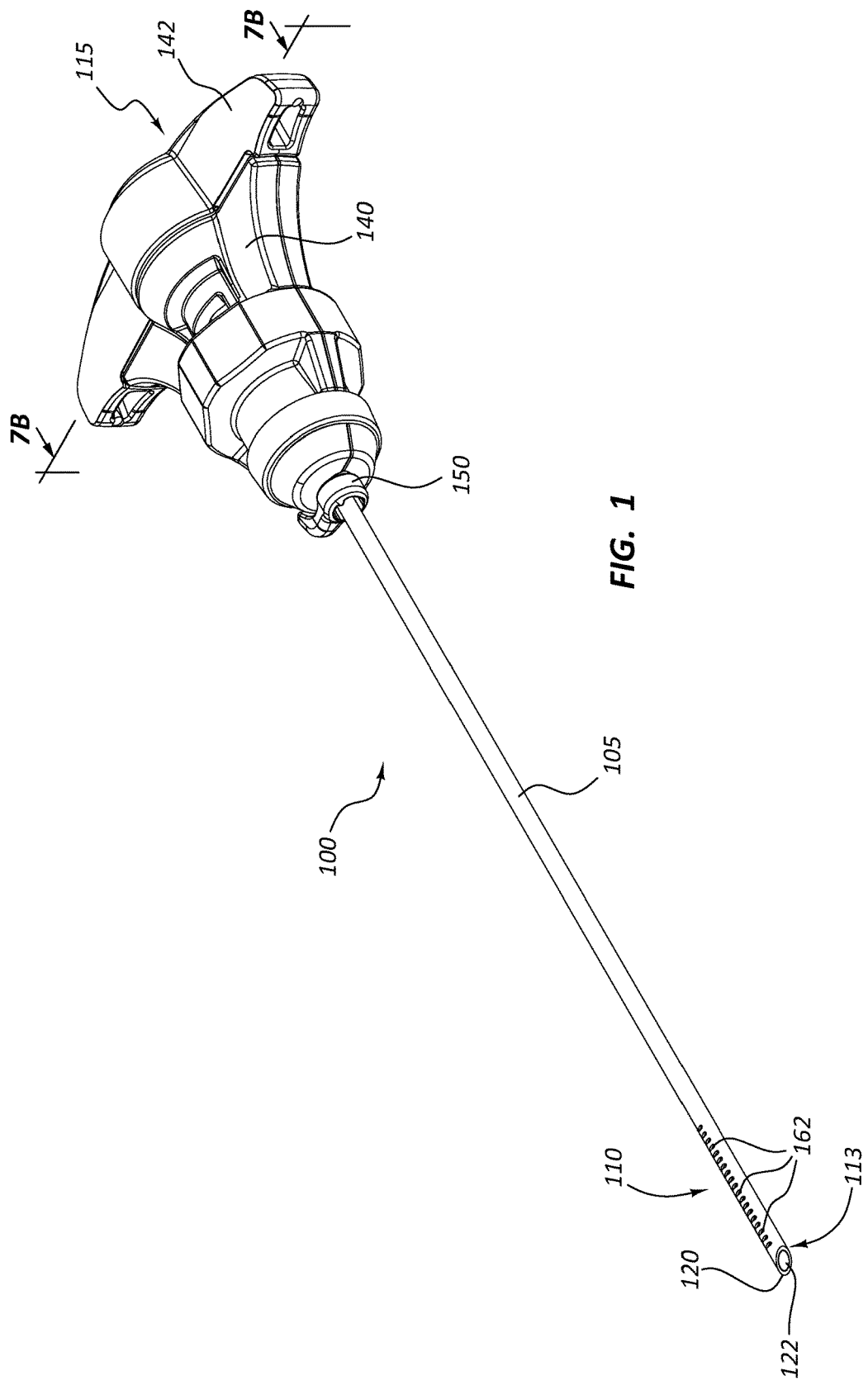
FIG. 1 is a perspective view of a medical device.

The various embodiments disclosed herein generally relate to medical devices including osteotomes. In certain embodiments, the medical device may include inner and outer members forming a working end portion. A distal end portion of the inner member may include a recessed portion, and a distal end portion of the outer member may include a plurality of slots. The recessed portion and the plurality of slots may interact to allow deflection of the working end portion (e.g., in a single plane). In some embodiments, the medical device may include an indicator, wherein the indicator is configured to communicate a direction of deflection of the working end portion to a practitioner or user.

In various embodiments, the medical device may include a torque release mechanism. The torque release mechanism may be configured to releasably uncouple a first portion of the medical device from a second portion of the medical device when an amount of torque applied to the medical device exceeds a predetermined value. The torque release mechanism may limit or prevent one or more components of the medical device from being compromised or damaged during use of the medical device.

It will be appreciated that various features are sometimes grouped together in a single embodiment, figure, or description thereof for the purpose of streamlining the disclosure. Many of these features may be used alone and/or in combination with one another.

Embodiments may be understood by reference to the drawings, wherein like parts are designated by like numerals throughout. It will be readily understood that the components of the present disclosure, as generally described and illustrated in the drawings herein, could be arranged and designed in a wide variety of different configurations. Thus, the following more detailed description of the embodiments of the apparatus is not intended to limit the scope of the disclosure, but is merely representative of possible embodiments of the disclosure. In some cases, well-known structures, materials, or operations are not shown or described in detail. While the various aspects of the embodiments are presented in drawings, the drawings are not necessarily drawn to scale unless specifically indicated.

The phrases "connected to," "coupled to," and "in communication with" refer to any form of interaction between two or more entities, including but not limited to mechanical, electrical, magnetic, electromagnetic, fluid, and thermal interaction. Two components may be coupled to each other even though they are not in direct contact with each other. For example, two components may be coupled to each other through an intermediate component.

The terms "proximal" and "distal" refer to opposite ends of a medical device, including the devices disclosed herein. As used herein, the proximal portion of a medical device is the portion nearest a practitioner during use, while the distal portion is the portion at the opposite end. For example, the proximal end of a medical device is defined as the end closest to the practitioner during utilization of the medical device. The distal end is the end opposite the proximal end, along the longitudinal direction of the medical device.

The term "resilient" refers to a component, device, or object having a particular shape that can then be elastically deformed into a different shape, but that may return to the original shape when unconstrained. For example, a resilient arm may have a first shape when unconstrained (i.e., when not engaged with a ridge of a female member) and, in use, the resilient arm may then be constrained (i.e., temporarily engaged with the ridge of the female member) to elastically deform the resilient arm into a second shape (i.e., displaced radially outward due to interaction with a portion of the ridge of the female member), then unconstrained (i.e., removed from engagement with the portion of the ridge of the female member) such that the resilient arm returns to its first shape or substantially returns to its first shape.

Figure 2:
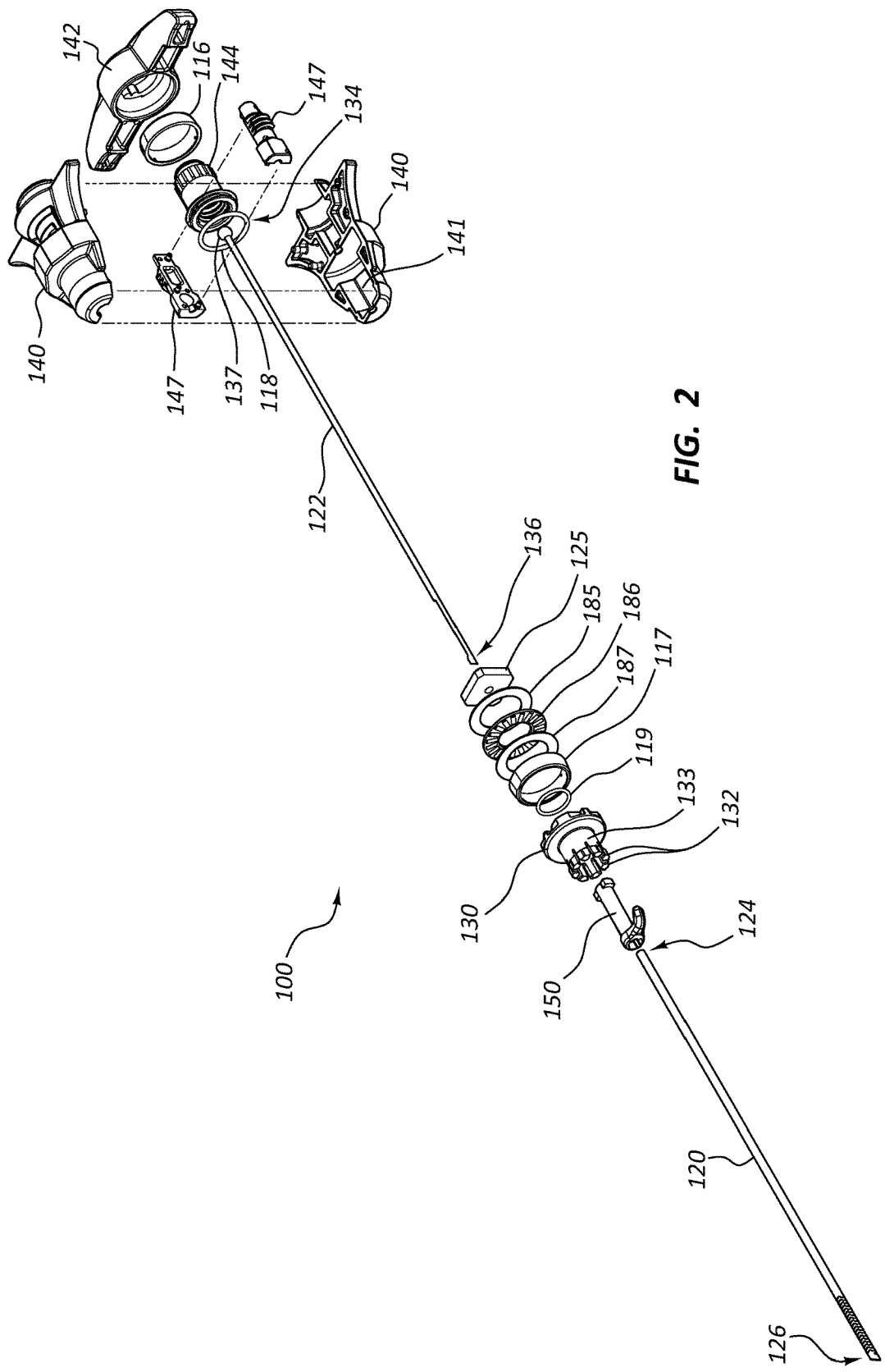
FIG. 2 is an exploded view of the medical device of FIG. 1.

FIG. 1 is a perspective view of a medical device 100 comprising an osteotome. FIG. 2 is an exploded view of the medical device 100. In some embodiments, the medical device 100 is configured for accessing the interior of a vertebral body and/or for creating a pathway in vertebral cancellous bone. In some embodiments, the pathway can receive bone fill material (e.g., bone cement). As depicted, the medical device 100 can include an extension member 105. The extension member 105 may be configured to be introduced through a pedicle of a vertebra.

The extension member 105 can include a working end portion 110 at or adjacent a distal end 113 of the extension member 105. In certain embodiments, the working end portion 110 of the extension member 105 may be configured to be progressively actuated (e.g., by a practitioner) such that at least a portion of the working end portion 110 bends, curves, and/or is deflected a selected degree. An indicator or tip indicator 150 can communicate or indicate to a practitioner the direction of the deflection of the working end portion 110. The working end portion 110 of the extension member 105 can also be configured to be rotated. Deflection and/or rotating of the working end portion 110 can form a curved pathway and/or a cavity in a vertebral body. For example, the deflection and/or rotating can form a curved pathway and/or a cavity in the direction of the midline of the vertebral body.

In various embodiments, the medical device 100 can be withdrawn and bone fill material may be introduced into the pathway and/or cavity (e.g., via a bone cement injection cannula). In various other embodiments, the medical device 100 may be configured for use as a cement injector. For example, upon formation of the curved pathway and/or the cavity, bone cement may be injected through at least a portion of the medical device 100 (e.g., through a lumen of the medical device 100).

The medical device 100 can further include a handle 115, wherein the handle 115 is coupled to a proximal end of the extension member 105. As described in further detail below, the extension member 105 can include a first or outer member 120 and a second or inner member 122. With reference to FIG. 2, the outer member 120 has a proximal end 124 and a distal end 126. An outer member plate 125 can be coupled, or configured to be coupled, to the proximal end 124 of the outer member 120. The inner member 122 also has a proximal end 134 and a distal end 136. A spherical portion 137 is coupled, or configured to be coupled, to the proximal end 134 of the inner member 122. Referring again to FIGS. 1 and 2, the extension member 105 can be coupled to the handle 115 to allow or permit a practitioner to drive the extension member 105 into a hard tissue (e.g., a bone) while contemporaneously, or substantially contemporaneously, actuating the working end portion 110 into a deflected or nonlinear configuration (see, e.g., FIG. 5C).

In some embodiments, the handle 115 may be formed from a polymer, a metal, or any other material that is suitable for withstanding impact forces that may be used to drive the medical device 100 into bone (e.g., via use of a hammer or similar device on the handle 115). In certain embodiments, the inner and outer members 120, 122 may be formed from a polymer, a metal, a metal ahoy, or any other suitable material. For example, the inner and outer members 122, 120 may be formed from a suitable metal alloy, such as stainless steel or a nickel titanium alloy (e.g., NITINOL). In various embodiments, the outer diameter of the outer member 120 may be from about 1.5 mm to about 5.0 mm, about 2.0 mm to about 4.0 mm, about 2.5 mm to about 3.5 mm, or another suitable outer diameter. In various embodiments, the inner diameter of the outer member 120 may be from about 1.0 mm to about 4.5 mm, about 1.5 mm to about 3.5 mm, about 2.0 mm to about 3.0 mm, or another suitable inner diameter.

As illustrated, the handle 115 can include a grip portion 140 and an actuator portion 142, wherein the actuator portion 142 can be rotatable relative to the grip portion 140. In some embodiments, the grip portion 140 may be configured to be grasped, gripped, and/or held by a user, and the actuator portion 142 may be configured to be actuated and/or rotated (with respect to the grip portion 140) by a user. The grip portion 140 can be coupled to the outer member 120. In some embodiments, the grip portion 140 can be coupled to the outer member 120 via the outer member plate 125 and/or the distal collar 130. The actuator portion 142 can be operably coupled to the inner member 122. In various embodiments, the actuator portion 142 can be coupled to the inner member 122 via the spherical portion 137, a female member 144, and/or a male member 147. The operation of each of the grip portion 140, the outer member 120, the outer member plate 125, and the distal collar 130 is discussed in further detail below. Likewise, the operation of each of the actuator portion 142, the inner member 122, the spherical portion 137, the female member 144, and the male member 147 is also discussed in further detail below.

With reference to FIG. 2, the medical device 100 can further include one or more O-rings 118, 119. The proximal O-ring 118 may be configured to be disposed around at least a portion of the female member 144 (e.g., a distal portion of the female member 144). The proximal O-ring 118 may compensate for tolerance or fit between the female member 144 and other components to create a smooth interaction between such components. The distal O-ring 119 may be configured to be disposed within a portion of the distal collar 130. For example, the distal O-ring 119 can be disposed within a locking member receiving portion 131 of the distal collar 130 (discussed in further detail below). The distal O-ring 119 may be configured to form a seal between the outer member plate 125 (e.g., a distal surface of the outer member plate 125) and the distal collar 130. The distal O-ring 119 may also compensate for differences in fit or tolerances between the components and facilitate smooth interaction of the components. In certain embodiments, the medical device 100 can further include a plurality of washers 185, 186, 187. The plurality of washers 185, 186, 187 may be configured to be disposed around the inner member 122 at a position proximal of the distal collar 130. Upon assembly of the medical device 100, the plurality of washers 185, 186, 187 can be disposed within at least a portion of the grip portion 140.

Figure 3:
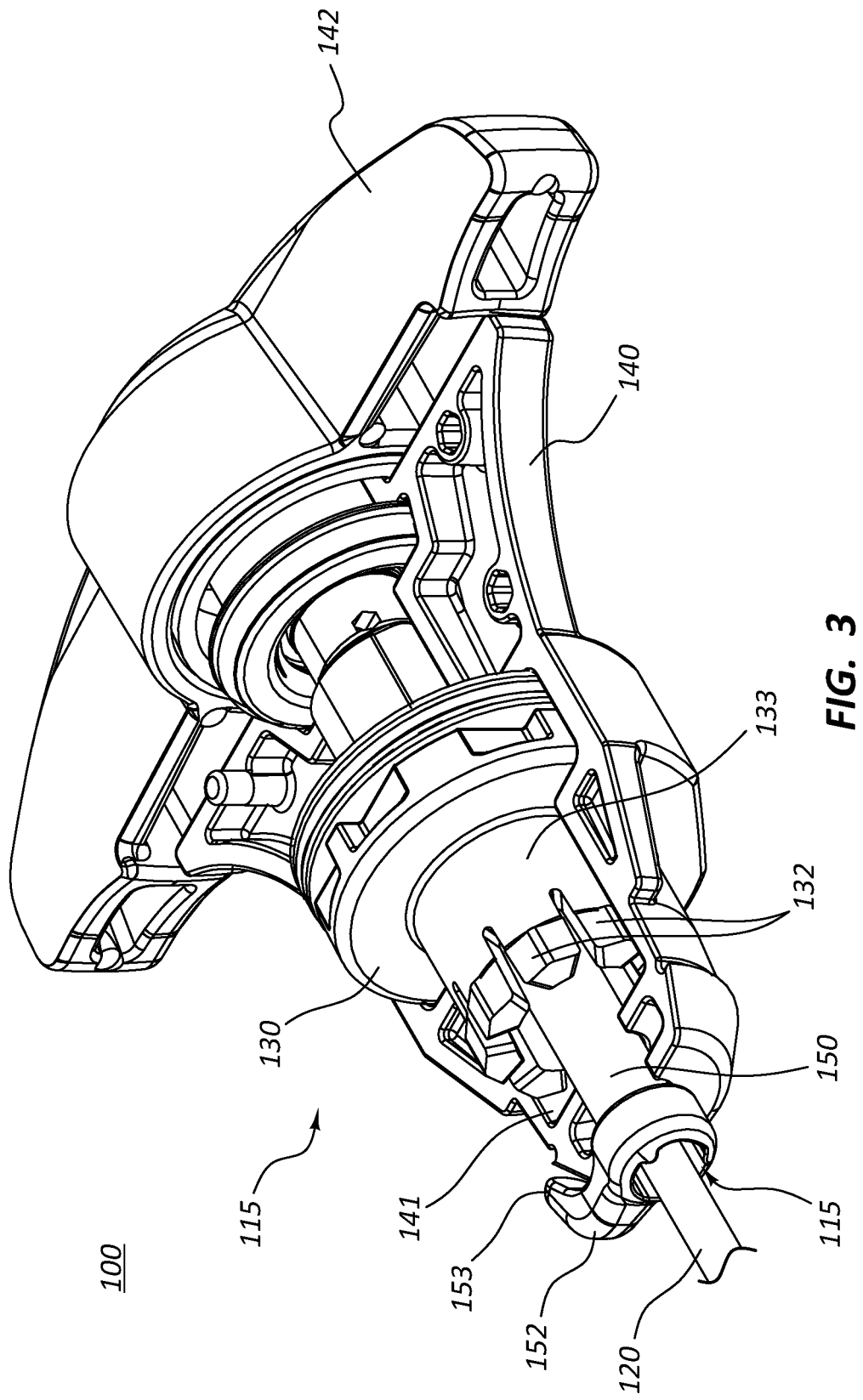
FIG. 3 is a detail view of a handle of the medical device of FIG. 1, wherein a portion of the handle has been removed.

FIG. 3 depicts a portion of the handle 115 of the medical device 100, wherein a portion (e.g., a half) of the grip portion 140 has been removed. Accordingly, at least a subset of the components of the medical device 100 that are disposed, or at least partially disposed, within the handle 115 are visible in this view. With reference to FIGS. 2 and 3, in some embodiments, the grip portion 140 may include a first portion or half and a second portion or half, wherein the first and second portions are configured to be coupled to each other to form the grip portion 140. In some embodiments, the first portion of the grip portion 140 and the second portion of the grip portion 140 may be held together by one or more of an adhesive, a fastener, a snap fit, and/or annular bands 116, 117. In some other embodiments, the grip portion 140 may be a single component or the grip portion 140 may include three, four, or more portions.

The distal collar 130 and the grip portion 140 can act as a torque limiter and/or release system. For example, if too much torque is applied to the outer member 120, the distal collar 130 and the grip portion 140 can be configured to allow the distal collar 130 to rotate with respect to the grip portion 140. In various embodiments, a portion of an inner surface 141 of the grip portion 140 can engage a portion of an outer surface of the distal collar 130, which is coupled to the proximal end 124 of the outer member 120 (e.g., via the outer member plate 125). The distal collar 130 can comprise a body 133 and a plurality of resilient members 132 that extend distally from a distal end of the body 133 of the distal collar 130.

An outer surface of each of the resilient members 132 can be substantially V-shaped. The outer surfaces of the resilient members 132 can engage a portion of the inner surface 141 of the grip portion 140, also referred to herein as the engagement surface 141. As illustrated, a contour or shape of the engagement surface 141 can substantially mirror the V-shape of the outer surfaces of the resilient members 132. In a locked configuration, the outer surfaces of the resilient members 132 engage the engagement surface 141. Rotation of the actuator portion 142 displaces the inner member 122 proximally or distally), and the degree of deflection of the working end portion 110 can be adjusted.

At a selected force, for example a torque from about 0.5 inch-pounds to about 7.5 inch-pounds, from about 0.5 inch-pounds to about 5.0 inch-pounds, from about 0.5 inch-pounds to about 2.5 inch-pounds, or another suitable amount of torque, the rotation of the distal collar 130 can exceed a predetermined limit. When too much torque (i.e., at a level at or above the predetermined limit) is provided to the outer member 120, the resilient members 132 can be displaced radially inward allowing the distal collar 130 to rotate or turn. Such rotation of the distal collar 130 may release from about 0.25 inch-pounds to about 10 inch-pounds of torque, from about 0.5 inch-pounds to about 7.5 inch-pounds of torque, from about 0.5 inch-pounds to about 5 inch-pounds of torque, or from about 0.5 inch-pounds to about 2.5 inch-pounds of torque, or another suitable amount of torque.

Referring again to FIG. 3, the medical device 100 can include the indicator 150. As stated above, the indicator 150 can be positioned or disposed to communicate or indicate (e.g., to a practitioner) the orientation (such as indicating the direction of deflection) of the working end portion 110. The indicator 150, as illustrated, includes a lumen 151. Accordingly, the indicator 150 can be disposed over and/or around at least a portion of the outer member 120. The indicator 150 can also include an indicator arm 152, wherein the indicator arm 152 extends radially outward from a longitudinal axis of the indicator 150. The indicator arm 152 can be disposed in the direction of deflection of the working end portion 110. As further detailed below, the working end portion 110 may be configured to deflect within a single plane and/or in a certain direction. Coupling the indicator 150 to the outer member 120 such that the outer member 120 and indicator 150 rotate together, may thus keep the indicator arm 152 aligned with the direction of deflection of the working end portion 110, even in instances wherein the outer member 120 and other components of the extension member 105 rotate with respect to the grip portion 140 due to slip or displacement of the torque limiting components described above.

As shown, an end portion of the indicator arm 152 can form a bend or curve. When the indicator 150 is coupled to the medical device 100, the end portion of the indicator arm 152 can bend or curve proximally toward the actuator portion 142. As illustrated, the indicator arm 152 is disposed around at least a portion of an outside surface of the grip portion 140. Stated another way, an inside surface of the indicator arm 152 (i.e., the surface of the indicator arm 152 that is disposed closest to a longitudinal axis of the outer member 120) may substantially conform to at least a portion of the outside surface of the grip portion 140.

In some embodiments, the indicator 150 may be formed from a polymer, a metal, or another suitable material. For example, the indicator 150 may be formed from molded acrylonitrile butadiene styrene (ABS), polycarbonate, nylon, etc.

FIG. 4A is a perspective view of the distal collar 130 and the indicator 150 in an uncoupled or unlocked configuration. FIG. 4B is a perspective view of the distal collar 130 and the indicator 150 in a coupled or locked configuration. The indicator 150 can include the lumen 151, wherein the lumen 151 can extend between a proximal end 153 and a distal end 154 of the indicator 150. The indicator arm 152 can extend from a position at or adjacent the distal end 154 of the indicator 150. Furthermore, the indicator 150 can also include a locking member 155, wherein the locking member 155 is disposed at or adjacent the proximal end 153 of the indicator 150. The locking member 155 can be configured to interlock and/or mate with a locking member receiving portion 131 of the distal collar 130.

The locking member 155 can include one or more extensions 156 that extend radially outward from the longitudinal axis of the indicator 150. In some embodiments, the locking member 155 may be configured to couple and/or secure the indicator 150 to the distal collar 130, for example, at the locking member receiving portion 131. As illustrated, the locking member receiving portion 131 can be substantially X-shaped or plus-sign-shaped. A first segment of the locking member receiving portion 131 can include an opening extending through the distal collar 130. A second segment of the locking member receiving portion 131 (that is rotationally offset by about 90° from the first segment of the locking member receiving portion 131) can include two indented portions 138 that are configured to receive and/or engage the two extensions 156 of the locking member 155. In some other embodiments, the locking member 155 and/or the locking member receiving portion 131 may be T-shaped, star-shaped, or otherwise suitably shaped. For example, the locking member 155 may include one, three, four, or more extensions 156. Likewise, the locking member receiving portion 131 may include one, three, four, or more indented portions.

In some embodiments, coupling the indicator 150 to the distal collar 130 may include proximally disposing the indicator 150 through the opening in the locking member receiving portion 131 such that the locking member 155 is disposed proximally of the locking member receiving portion 131. The indicator 150 can then be rotated around its longitudinal axis (e.g., about 90° as indicated in FIGS. 4A and 4B) such that the extensions 156 are substantially aligned with the indented portions 138 of the locking member receiving portion 131. The indicator 150 can then be displaced distally in relation to the distal collar 130 such that the extensions 156 are disposed within each of the indented portions 138 of the locking member receiving portion 131.

As described above, the distal collar 130 couples, or is configured to couple, both the outer member 120 and the indicator 150. For instance, in some instances the outer member plate 125 may mate with a recess on the distal collar 130 when the outer member 120 extends through the lumen 151 of the indicator 150. The indicator 150 can be coupled to the distal collar 130 such that the indicator arm 152 of the indicator 150 is substantially aligned with the direction of the deflection of the working end portion 110. Furthermore, upon rotation of the distal collar 130 (e.g., upon the release of excess torque) the indicator arm 152 of the indicator 150 can remain substantially aligned with the direction of the deflection of the working end portion 110. Rotation of the distal collar 130 can result in or effect rotation of each of the indicator 150 and the outer member 120.

Figure 5A:
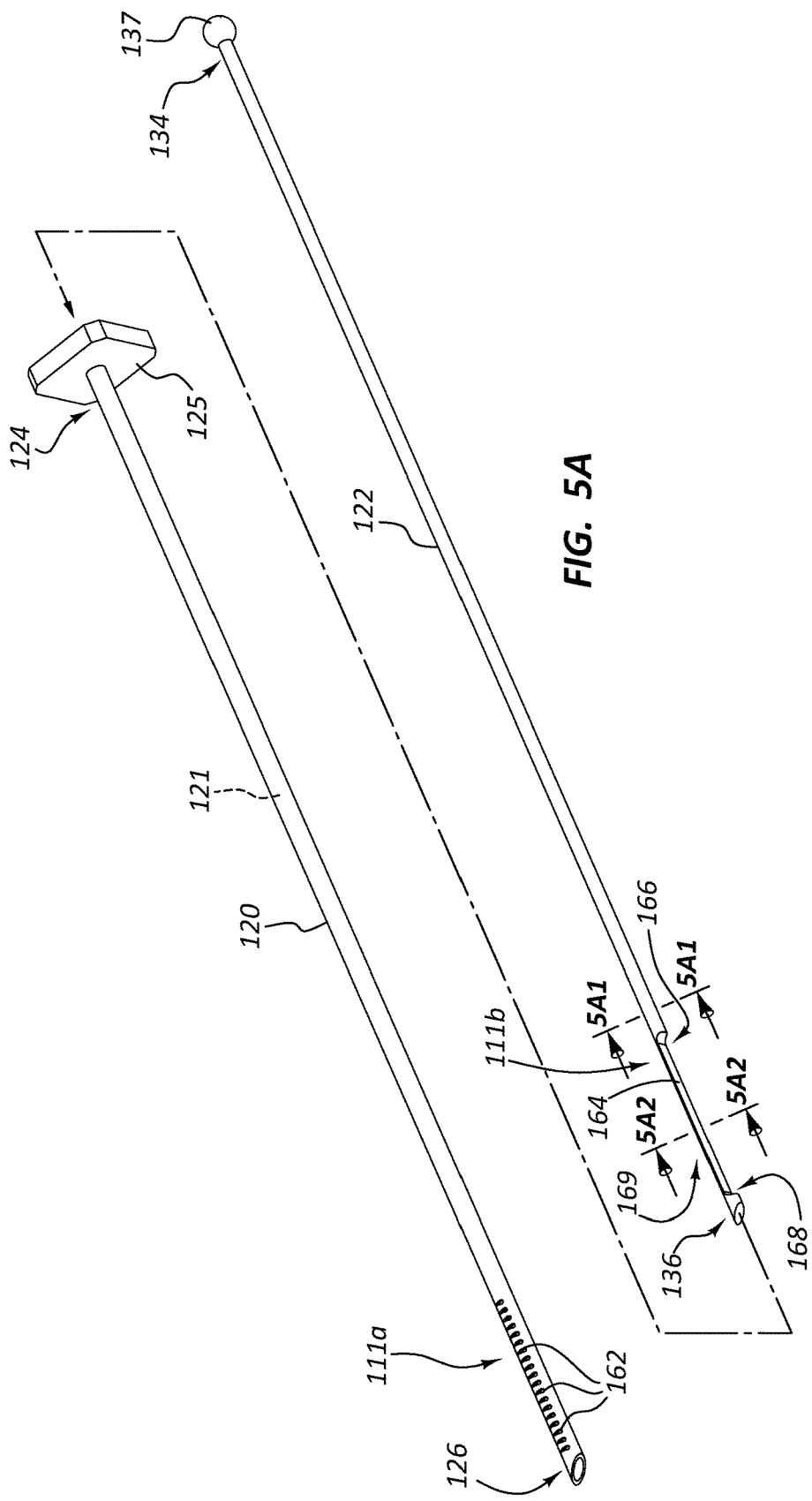
FIG. 5A is a perspective view of an inner member and an outer member of the medical device of FIG. 1 in an uncoupled configuration.

FIG. 5A is a perspective view of the outer member 120 and the inner member 122. FIG. 5B is a cross-sectional view of the working end portion 110 of the medical device 100 of FIG. 1 in an undeflected configuration (e.g., a linear configuration). FIG. 5C depicts the working end portion 110 of FIG. 5B in a deflected configuration (e.g., a nonlinear configuration). As indicated by the arrow in FIG. 5A, the inner member 122 may be disposed within the lumen 121 of the outer member 120. As discussed above, the outer member plate 125 can be coupled to the proximal end 124 of the outer member 120. Additionally, the spherical portion 137 can be coupled to the proximal end 134 of the inner member 122.

As shown, the outer member 120 can include an outer working end portion 111a, and the inner member 122 can include an inner working end portion 111b. In some embodiments, the outer working end portion 111a and the inner working end portion 111b can cooperate to form the working end portion 110. The outer working end portion 111a can include a plurality of slots or notches 162 (for clarity, only a subset of the slots 162 are labelled in the figures). The inner working end portion 111b of the inner member 122 can include a recessed portion 164. In some embodiments, the working end portion 110 of the extension member 105 may be bent, curved, and/or deflected by cooperation between the plurality of slots 162 of the outer working end portion 111a and the recessed portion 164 of the inner working end portion 111b (see, e.g., FIG. 5C).

The working end portion 110 (including each of the outer and inner working end portions 111a, 111b) may be capable of bending, curving, and/or being deflected in a substantially tight radius. In the deflected configuration, a distal end 113 of the working end portion 110 can be displaced at least about 5°, at least about 10° at least about 20°, at least about 30°, at least about 40°, at least about 50°, at least about 60°, at least about 70°, at least about 80°, at least about 90°, at least about 100° or more degrees relative to a longitudinal axis of a portion of the extension member 105 proximal of the working end portion 110. In some embodiments, in the deflected configuration, the distal end 113 of the working end portion 110 can be displaced relative, to the longitudinal axis of a portion of the extension member 105 proximal of the working end portion 110 from about 50° to about 110°, from about 60° to about 100°, or from about 70° to about 90° relative to the longitudinal axis of a portion of the extension member 105 proximal of the working end portion 110. Stated another way, in the undeflected configuration the distal end 113 of the working end portion 110 can be disposed substantially along the longitudinal axis of the extension member 105. In the deflected configuration, however, the distal end 113 of the working end portion 110 can be displaced away from the longitudinal axis of the extension member 105 (i.e., by a predetermined number of degrees away from the longitudinal axis).

The slots 162 may be any slots that are perpendicular or angled relative to the longitudinal axis of the outer member 120. As shown in FIG. 5B, the recessed portion 164 of the inner member 122 may be disposed on an opposite side, or a substantially opposite side, of the working end portion 110 relative to the plurality of slots 162 of the outer member 120. In other words, the recessed portion 164 of the inner member 122 can be substantially oriented in opposition to the plurality of slots 162 of the outer member 120 (i.e., when the inner member 122 is coupled to the outer member 120 as illustrated).

The configuration of the inner member 122 including the recessed portion 164, as described herein and/or as illustrated, may inhibit or prevent breaking, crimping, folding, or other failure of the inner working end portion 111b during bending, curving, and/or deflection of the working end portion 110. In some embodiments, when the inner member 122 is constrained (e.g., upon deflection of the working end portion 110) a force of about 32 pounds may be exerted by the working end portion 110. The inner member 122 and/or the recessed portion 164 may be configured to exert a force of greater than about 20 pounds, greater than about 26 pounds, greater than about 38 pounds, greater than about 44 pounds, or a force of another suitable magnitude.

In certain embodiments, the distal end 126 of the outer member 120 can be coupled to the distal end 136 of the inner member 122, for example, at a coupling portion 160. In certain other embodiments, a coupling portion (analogous to the coupling portion 160) may be disposed more proximally relative to the distal end 113 or the working end portion 110 than the illustrated coupling portion 160. In various embodiments, the outer member 120 may be welded to the inner member 122 at the coupling portion 160 (e.g., the outer member 120 may be laser-welded to the inner member 122). Other mechanisms of coupling the outer member 120 to the inner member 122 are also within the scope of this disclosure, e.g., glue, interlocking components, etc. Accordingly, when the inner member 122 is displaced or translated in a proximal direction (i.e., by rotation of the actuator portion 142), the outer member 120 may be bent, curved, or deflected as depicted in FIG. 5C. Furthermore, rotation of the actuator portion 142 a selected amount can bend, curve, and/or deflect the working end portion 110 to a selected degree.

As depicted, the recessed portion 164 may allow or permit the inner working end portion 111b of the inner member 122 to bend, curve, and/or be deflected. The direction of bending, curving, and/or deflection of the inner working end portion 111b may limited or restricted, however, by the location or position of the slots 162 of the outer member 120. In some embodiments, the curvature of the working end portion 110 may be controlled or limited by the spacing, shape, and/or angle of the slots 162.

As the inner member 122 is displaced in a proximal direction with respect to a proximal portion of the outer member 120, the working end portion 110 may transition from a linear configuration (such as shown in FIG. 5B) to a curved configuration in which the slots 162 of the outer portion 120 are disposed on the concave side of the bend (such as shown in FIG. 5C). Distal displacement of the inner member 122 with respect to a proximal portion of the outer member 120 causes the working end portion 110 to curve in the opposite direction, such that the slots 162 will be disposed on the convex side of the curve. The recessed portion 164 may flex within the outer member 120 as shown, for example, in FIGS. 5B and 5C. As also discussed below, the distal coupling of the outer member 120 and inner member 122, together with the relative positions of the slots 162 and the recessed portion may thus restrict the bending of the working portion to bending within a single plane.

As illustrated, each of the distal end 126 of the outer member 120 and the distal end 136 of the inner member 122 is beveled. The beveled configuration can be used or aid in entry of at least a portion of the medical device 100 (e.g., the working end portion 110) through the cortical bone of a vertebral body. In certain embodiments, only one of the distal end 126 of the outer member 120 or the distal end 136 of the inner member 122 may be beveled.

In some embodiments, the inner member 122 and/or the inner working end portion 111b may be machined to form the recessed portion 164. Other suitable methods (e.g., molding) may also be used to form the recessed portion 164. In certain embodiments, the outer member 120 may be laser-cut to form the plurality of slots 162. Other suitable methods may also be used to form the plurality of slots 162.

FIG. 5A1 is a cross-sectional view of the inner member 122 through line 5A1-5A1 of FIG. 5A. FIG. 5A2 is a cross-sectional view of the inner member 122 through line 5A2-5A2 of FIG. 5A. With reference to FIG. 5A1, a cross-section transverse to a longitudinal axis of the inner member 122 at a position proximal of the recessed portion 164 can be substantially circular. In some other embodiments, a cross-section of the inner member 122 at this position may be otherwise shaped; for example, the cross-section may be square, rectangular, oval, etc. With reference to FIG. 5A2, a cross-section transverse to the longitudinal axis of the inner member 122 at the recessed portion 164 can be substantially segmental (i.e., a segment of the circle depicted in FIG. 5A1). In some other embodiments, a cross-section of the inner member 122 at the recessed portion 164 may be otherwise shaped; for example, the cross-section may be a portion or segment of a square, a rectangle, an oval, etc.

With reference to FIGS. 1-5C the osteotome or medical device 100 (e.g., a medical device for treating a hard tissue) can include a handle 115 and an extension member 105 operably coupled to the handle 115. The extension member 105 can include an inner member 122 disposed within at least a portion of an outer member 120. Again, in some embodiments, actuation or rotation of at least a portion of the handle 115 may be configured to bend, curve, and/or deflect a working end portion 110 of the extension member 105. The working end portion 110 can be disposed adjacent a distal end 113 of the extension member 105 (see, e.g., FIG. 1).

The medical device 100 can further include an indicator 150 operably coupled to the outer member 120. In certain embodiments, the indicator 150 can communicate a direction of deflection of the working end portion 110 to a user. The indicator 150 can include an elongate body 157 and a locking member 155 coupled to a proximal end of the elongate body 157. In various embodiments, the locking member 155 may be configured to operably couple the indicator 150 to the outer member 120. The indicator 150 can further include an indicator arm 152 coupled to a distal end of the elongate body 157. The indicator arm 152 can extend radially outward from a longitudinal axis of the elongate body 157. In some embodiments, the indicator arm 152 may be configured to communicate the direction of deflection of the working end portion 110 to the user.

The handle 115 can include an actuator portion 142 operably coupled to the working end portion 110. The handle 115 can further include a grip portion 140 disposed distal of and operably coupled to the actuator portion 142. In certain embodiments, actuation and/or rotation of the actuator portion 142 may be configured to longitudinally displace the inner member 122 relative to the outer member 120 such that the working end portion 110 can transition between a deflected configuration and an undeflected configuration, or vice versa.

The locking member 155 of the indicator 150 can be disposed within at least a portion of the grip portion 140. Furthermore, the indicator arm 152 can be disposed outside or external of the grip portion 140 such that the indicator arm 152 is visible to the user. The indicator arm 152 can extend around at least a portion of an outer surface of the grip portion 140. In various embodiments, the indicator 150 and/or the indicator arm 152 may be a first color (e.g., white) and the grip portion 140 may be a second color (e.g., blue) such that a visibility (i.e., to a user) of the indicator 150 and/or the indicator arm 152 may be enhanced.

The medical device 100 may further include a distal collar 130 disposed within and coupled to the handle 115. The distal collar 130 may include an outer member receiving portion or outer member plate receiving portion 135 configured to couple an outer member plate 125 and/or a proximal end 124 of the outer member 120 to the distal collar 130. The distal collar 130 may further include the locking member receiving portion 131 configured to couple a proximal end 153 and/or a locking member 155 of the indicator 150 to the distal collar 130. In some embodiments, the outer member 120 and the indicator 150 may not be rotatable relative to the distal collar 130 (e.g., due at least in part to the coupling of each of the outer member 120 and the indicator 150 to the distal collar 130).

The locking member 155 can be coupled to the proximal end 153 of the indicator 150. In turn, the locking member 155 can include at least one extension 156 extending radially outward from a longitudinal axis of the indicator 150. As depicted, the locking member 155 can include two extensions 156, wherein each of the two extensions 156 is disposed on an opposite side of the elongate body 157 of the indicator 150 (see, e.g., FIGS. 4A and 4B). In certain embodiments, the at least one extension 156 may engage, or be configured to engage, the locking member receiving portion 131 such that the indicator 150 is not substantially rotatable relative to the distal collar 130.

In various embodiments, the medical device 100 may include a handle 115 and an extension member 105 coupled to, and extending distally from, the handle 115. As described above, the extension member 105 may include the outer member 120. Furthermore, the outer member 120 may include a lumen 121 extending from at least a distal end 126 of the outer member 120. In some embodiments, the lumen 121 may extend from a distal end 126 to a proximal end 124 of the outer member 120. Additionally, the plurality of slots or notches 162 can be disposed in a wall of the outer member 120. For example, the plurality of slots 162 may be disposed along at least a portion of a length of the distal end portion of the outer member 120.

The extension member 105 can further include the inner member 122. The inner member 122 can be disposed within at least a portion of the outer member 120. Furthermore, the inner member 122 can include a recessed portion 164. The recessed portion 164 can be disposed along at least a portion of a length of a distal end portion of the inner member 122. The distal end portions of the outer and inner members 120, 122 (including the plurality of slots 162 and the recessed portion 164, respectively) can cooperate and/or interact to form the working end portion 110 of the extension member 105. In certain embodiments, the plurality of slots 162 can be radially offset from the recessed portion 164. For example, the plurality of slots 162 may be disposed on an opposite side (or substantially opposite side) of the working end portion 110 from the recessed portion 164. Stated another way, the plurality of slots 162 may be circumferentially offset from the recessed portion 164, meaning offset along a circumference of the working end portion 110. Additionally, the plurality of slots 162 and the recessed portion 164 can cooperate and/or interact to allow or permit deflection of the working end portion 110 (e.g., upon actuation or rotation of the handle 115). An arrangement of the plurality of slots 162 disposed on the opposite side from the recessed portion may be configured to limit deflection of the working end portion to a single plane.

In some embodiments, a length of the recessed portion 164 may be substantially equal to a length of the portion of the inner member 122 including the plurality of slots 162. Stated another way, the distance between the distal-most slot 162 and the proximal-most slot 162 may be substantially equal to the distance between the distal end 168 of the recessed portion 164 and the proximal end 166 of the recessed portion 164. In some other embodiments, the length of the recessed portion 164 may be greater than the length of the portion of the inner member 122 including the plurality of slots 162. In yet some other embodiments, the length of the recessed portion 164 may be less than the length of the portion of the inner member 122 including the plurality of slots 162.

Again, in various embodiments, the plurality of slots 162 and/or the recessed portion 164 can substantially limit deflection of the working end portion 110 to a single plane. Stated another way, the working end portion 110 may be configured to bend, curve, and/or be deflected in only a single plane (i.e., due at least in part to the plurality of slots 162 and/or the recessed portion 164).

The distal end 126 or distal end portion of the outer member 120 can be coupled (e.g., fixedly coupled) to the distal end 136 or distal end portion of the inner member 122 (e.g., via a weld). Actuation of the handle 115 can longitudinally displace the inner member 122 relative to the outer member 120. Such longitudinal displacement can transition the working end portion 110 from an undeflected configuration to a deflected configuration. In certain embodiments, the fixed coupling of the outer member 120 to the inner member 122 can inhibit or limit rotational movement of the outer member 120 relative to the inner member 122.

The inner member 122 can include a wire or be formed from a wire. In some embodiments, a thickness of the wire distal of the recessed portion 164 may be greater than a thickness of the wire at the recessed portion 164. Likewise, a thickness of the wire proximal of the recessed portion 164 may be greater than the thickness of the wire at the recessed portion 164. Furthermore, the recessed portion 164 can include a distal end 168, a medial portion 169, and a proximal end 166. With reference to FIG. 5A, the medial portion 169 can have a first thickness. Furthermore, the portion of the inner member 122 disposed proximal of the recessed portion 164 can have a second thickness, and a portion of the inner member 122 disposed distal of the recessed portion 164 can have a third thickness. In the illustrated embodiment, each of the second and third thicknesses is greater than the first thickness. Stated another way, the thickness of the recessed portion 164 (or at least a portion of the recessed portion 164) is less than a thickness of the remaining portions of the inner member 122 (or at least portions of the remaining portions of the inner member 122).

Additionally, the thickness of the inner member 122 can transition from the first thickness to the second thickness at the proximal end 166 of the recessed portion 164, and the thickness of the inner member 122 can transition from the first thickness to the third thickness at the distal end 168 of the recessed portion 164. In some embodiments, the medial portion 169 and/or the recessed portion 164 may be configured to be bent, curved, or deflected, while the portions of the inner member 122 proximal and/or distal of the recessed portion 164 may not be configured to be bent, curved, or deflected. Furthermore, the medial portion 169 and/or the recessed portion 164 can be resilient, as described above.

Figure 6A:
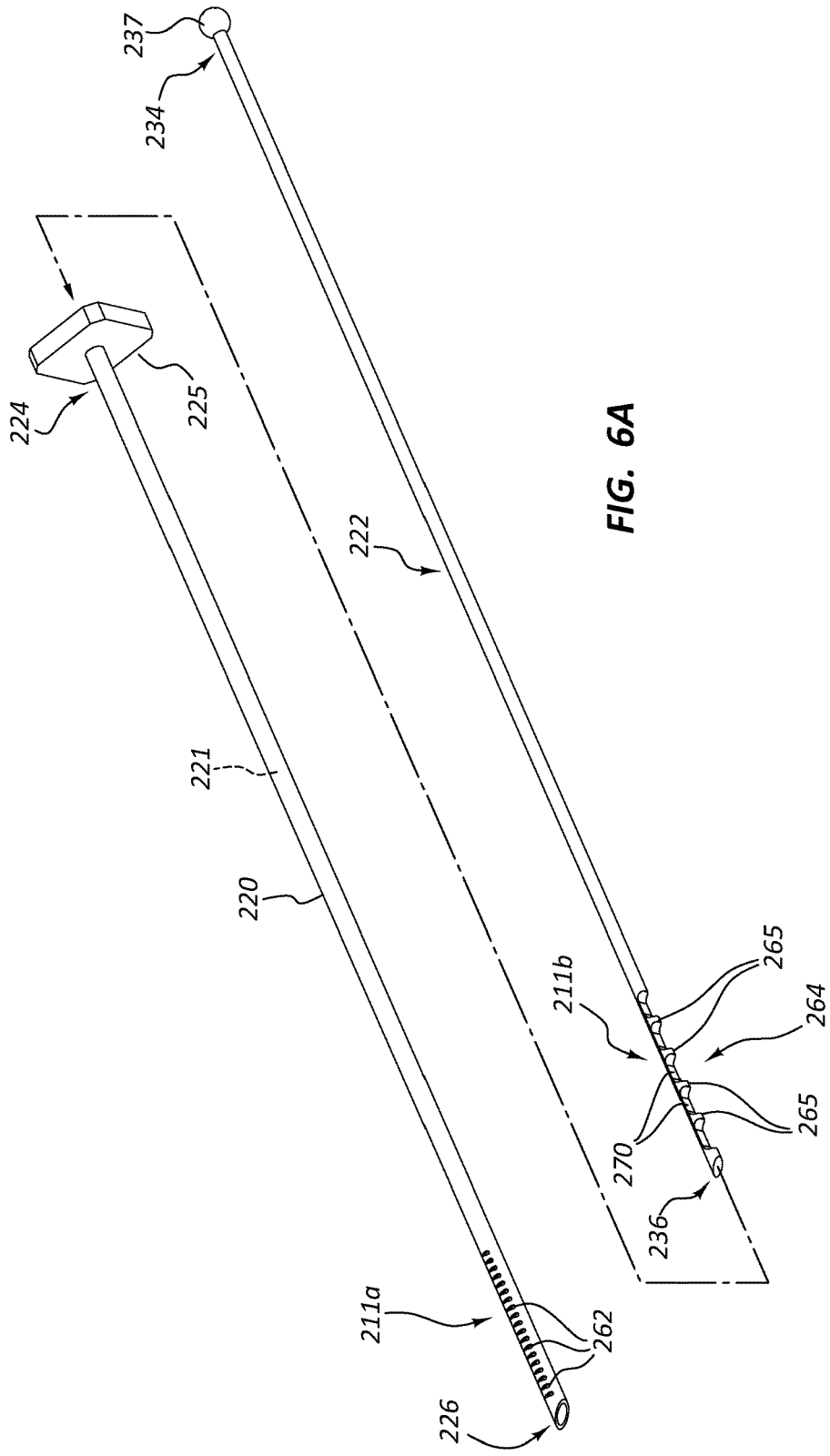
FIG. 6A is a perspective view of another embodiment of an inner member and an outer member in an uncoupled configuration.
Figure 6C:
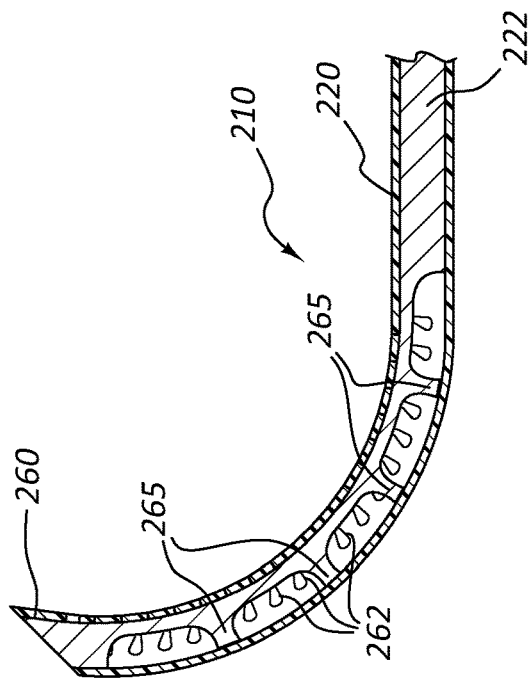
FIG. 6C is a cross-sectional view of the working end portion of FIG. 6B in a deflected configuration.
Figure 6B:
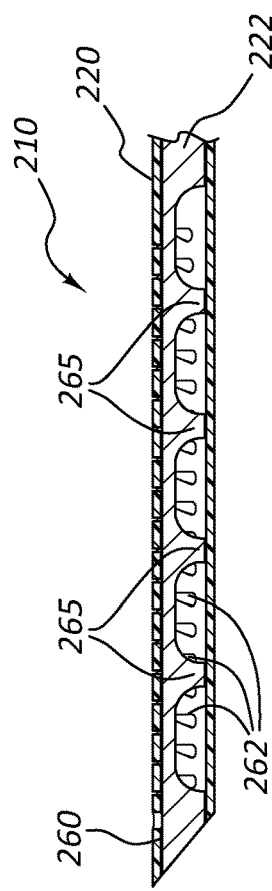
FIG. 6B is a cross-sectional view of a working end portion, analogous to the working end portion of FIG. 5B, including the inner and outer members of FIG. 6A in an undeflected configuration.

FIGS. 6A-6C illustrate an outer member 220 and an inner member 222 that can, in certain respects, resemble the outer member 120 and the inner member 122 described in connection with FIGS. 1, 2, and 5A-5C. It will be appreciated that all the illustrated embodiments may have analogous features. Accordingly, like features are designated with like reference numerals, with the leading digits incremented to "2." For instance, the slots are designated as "162" in FIGS. 5A-5C, and analogous slots are designated as "262" in FIGS. 6A-6C. Relevant disclosure set forth above regarding similarly identified features thus may not be repeated hereafter. Moreover, specific features of the outer member 120 and the inner member 122 and related components shown in FIGS. 1, 2, and 5A-5C may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the outer member 220 and the inner member 222 of FIGS. 6A-6C. Any suitable combination of the features, and variations of the same, described with respect to the outer member 120 and the inner member 122 and components illustrated in FIGS. 1, 2, and 5A-5C can be employed with the outer member 220 and the inner member 222 and components of FIGS. 6A-6C, and vice versa. This pattern of disclosure applies equally to further embodiments depicted in subsequent figures and described hereafter.

FIG. 6A is a perspective view of the outer member 220 and the inner member 222. FIG. 6B is a cross-sectional view of a working end portion 210 of an extension member of a medical device or osteotome (analogous to the extension member 105 and the medical device 100) in an undeflected configuration. FIG. 6C depicts the working end portion 210 of FIG. 6B in a deflected configuration. As indicated by the arrow in FIG. 6A, the inner member 222 may be disposed within a lumen 221 of the outer member 220. An outer member plate 225 can be coupled to a proximal end 224 of the outer member 220, and a spherical portion 237 can be coupled to a proximal end 234 of the inner member 222.

As shown, the outer member 220 can include an outer working end portion 211a, and the inner member 222 can include an inner working end portion 211b. In some embodiments, the outer working end portion 211a and the inner working end portion 211b can cooperate to form the working end portion 210. The outer working end portion 211a can include a plurality of slots or notches 262. The inner working end portion 211b can include a reinforced recessed portion 264.

In contrast to the recessed portion 164 discussed above in reference to FIGS. 5A-5C, the reinforced recessed portion 264 can include a plurality of reinforcement or support members 265. As illustrated, the recessed portion 264 includes four reinforcement members 265. In some embodiments, the recessed portion 264 may include one, two, three, five, six, or more reinforcement members 265. The one or more reinforcement members 265 can strengthen and/or support the recessed portion 264. For example, when a force is exerted on the recessed portion 264 (e.g., during bending, curving, and/or deflection of the working end portion 210), the one or more reinforcement members 265 tend to maintain the radial position of the recessed portion within the outer member 220. This may, in turn, inhibit or prevent the recessed portion 264 from buckling, crimping, or otherwise failing. The one or more reinforcement members 265 can extend across the space between a surface of the recessed portion 264 and an inside surface of the outer member 220 when the inner member 222 is disposed within the outer member 220 as illustrated in FIG. 6B. Accordingly, the one or more reinforcement members 265 can support the recessed portion 264. Analogously, the one or more reinforcement members 265 can support a portion of the outer member 220 that is disposed adjacent the recessed portion 264.

As shown in FIG. 6B, the reinforced recessed portion 264 of the inner member 222 may be disposed on an opposite side of the working end portion 210 relative to the plurality of slots 262 of the outer member 220. The configuration of the inner member 222, the recessed portion 264, and the reinforcement member 265, as described herein and/or as illustrated, may inhibit or limit breaking, crimping, folding, or other failure of the inner working end portion 211b during bending, curving, and/or deflection of the working end portion 210.

The distal end 226 of the outer member 220 can be coupled to the distal end 236 of the inner member 222 at a coupling portion 260. Accordingly, when the inner member 222 is displaced or translated in a proximal direction (i.e., by rotation of an actuator portion analogous to the actuator portion 142), the outer member 220 may be bent, curved, or deflected as depicted in FIG. 6C. Furthermore, rotation of the actuator portion a selected amount can bend, curve, and/or deflect the working end portion 210 to a selected degree.

As depicted, the recessed portion 264 may allow or permit the inner working end portion 211b of the inner member 222 to bend, curve, and/or be deflected in multiple directions. The direction of bending, curving, and/or deflection of the inner working end portion 211b may be limited or restricted, however, by the location or position of the slots 262 of the outer member 220. In some embodiments, the curvature of the working end portion 210 may be controlled or limited by the spacing, shape, and/or angle of the slots 262. As illustrated, each of the distal end 226 of the outer member 220 and the distal end 236 of the inner member 222 is beveled. In certain embodiments, only one of the distal end 226 of the outer member 220 or the distal end 236 of the inner member 222 may be beveled.

In certain embodiments, the one or more reinforcement members 265 can be disposed within at least a portion of the recessed portion 264. For example, the reinforcement member 265 can extend from a surface 270 of the recessed portion 264 to a position at or adjacent an inner surface of the outer member 220. The one or more reinforcement members 265 can be integrally formed with the inner member 222. In some other embodiments, the one or more reinforcement members 265 and the inner member 222 may be discrete components.

Figure 7A:
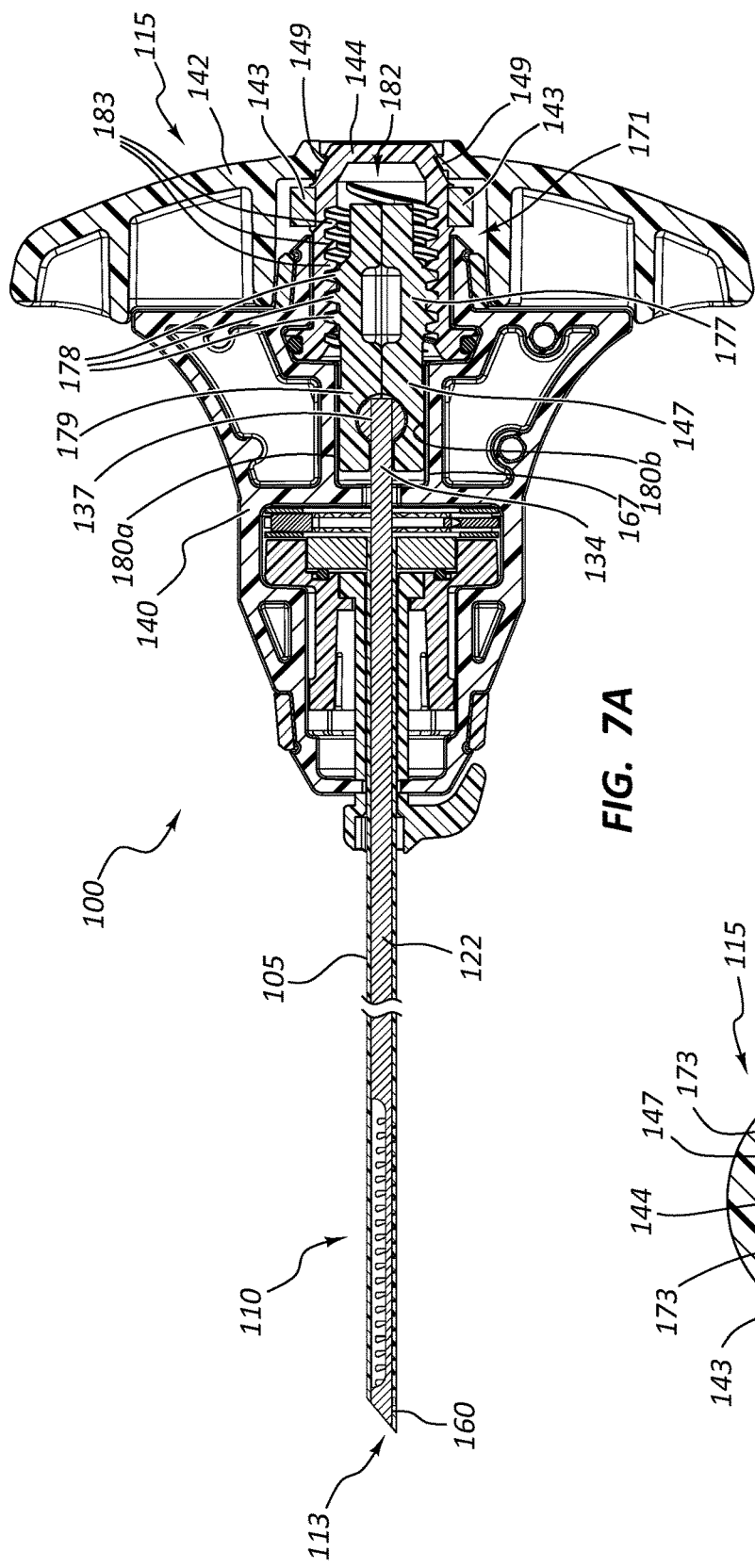
FIG. 7A is a cross-sectional view of a portion of the medical device of FIG. 1.
Figure 7B:
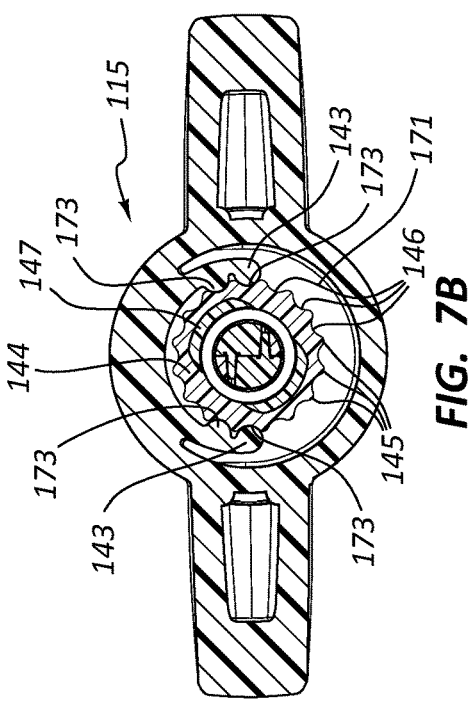
FIG. 7B is a cross-sectional view of the medical device of FIG. 1 through line 7B-7B.
Figure 8B:
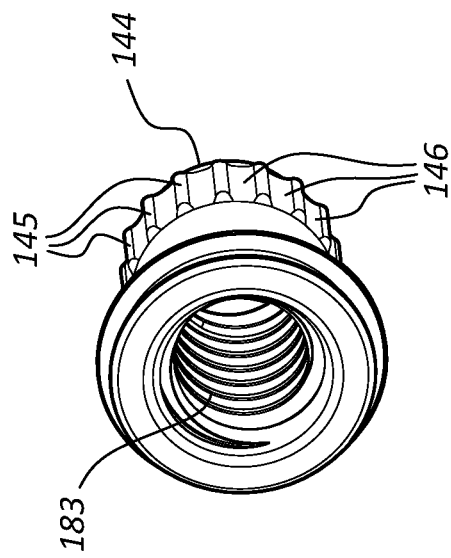
FIG. 8B is a perspective view of a distal end of a female member.
Figure 8A:
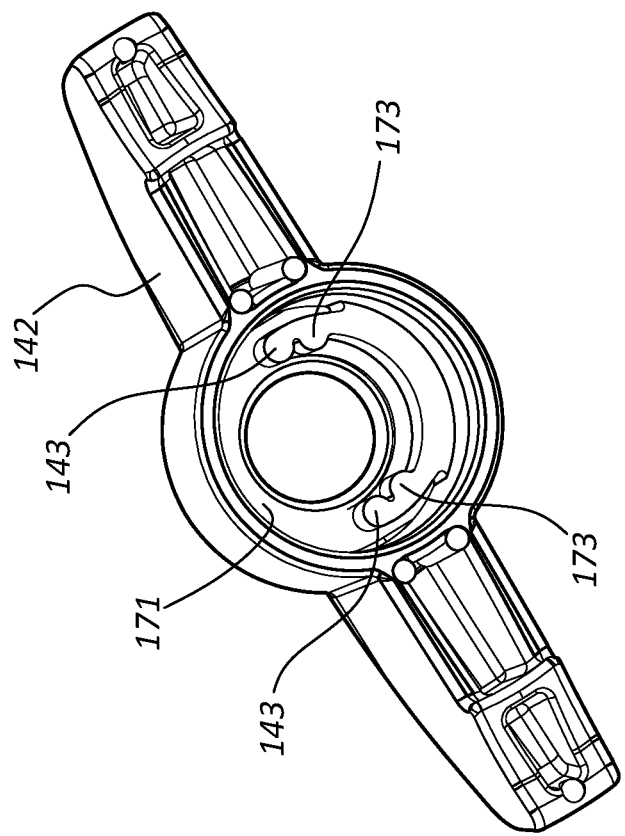
FIG. 8A is a perspective view of a distal end of an actuator portion.

FIG. 7A is a cross-sectional view of a portion of the medical device 100 of FIG. 1. FIG. 7B is a cross-sectional view of the medical device 100 through line 7B-7B of FIG. 1. As depicted, the medical device 100 can include the handle 115. Furthermore, the handle 115 can include the actuator portion 142 and the grip portion 140. In some embodiments, rotation of the actuator portion 142 relative to the grip portion 140 can bend, curve, and/or deflect the working end portion 110 of the extension member 105. The actuator portion 142 can be coupled to the female member 144, wherein the female member 144 can be at least partially disposed within an inner cavity 171 of the actuator portion 142. For example, the actuator portion 142 may be coupled to the female member 144 by means of a snap-fit joint 149 at a proximal end of each of the actuator portion 142 and the female member 144. At a position distal of the snap-fit joint 149, the actuator portion 142 can include one or more resilient arms 143 disposed within the inner cavity 171 of the actuator portion 142. As illustrated, the actuator portion 142 includes two resilient arms 143, wherein the resilient arms 143 are disposed in opposition, or substantial opposition, to each other within the inner cavity 171. In some embodiments, the actuator portion 142 may include three, four, or more resilient arms 143. The disposition of the resilient arms 143 within the actuator portion 142 can vary. For example, the resilient arms 143 may be substantially evenly spaced around a circumference of the inner cavity 171. In another example, the resilient arms 143 may be unevenly spaced or otherwise disposed within the actuator portion 142.

Furthermore, one or more teeth 173 may extend radially inward from the one or more resilient arms 143. As illustrated, each of the one or more resilient arms 143 includes two teeth 173 (e.g., rounded teeth 173). In some embodiments, the one or more resilient arms 143 may include one, three, four, or more teeth 173. In some other embodiments, a first resilient arm may include a different number of teeth than a second resilient arm (e.g., the first resilient arm may include one tooth, and the second resilient arm may include three teeth). The shape of the one or more teeth 173 may vary. For example, the teeth 173 may be semicircular, triangular, or otherwise suitably shaped.

The female member 144 can include a plurality of ridges 145 and grooves 146. Stated another way, an outside surface of the female member 144 may be gear-like. The ridges 145 may extend radially outward from the outside surface of the female member 144 and/or in relation to the grooves 146. The ridges 145 and grooves 146, as illustrated, may be configured to engage or interact with the teeth 173 of the actuator portion 142. The engagement of at least a portion of the ridges 145 and/or the grooves 146 with at least a portion of the teeth 173 can further couple the actuator portion 142 to the female member 144. This engagement can allow for or drive rotation of the female member 144 upon rotation of the actuator portion 142.

Additionally, the male member 147 can be coupled to the inner member 122. As illustrated, the proximal end 134 of the inner member 122 is coupled to the male member 147. For example, the spherical portion 137, which is coupled to the proximal end 134 of the inner member 122, can be disposed within a portion of the male member 147 such that the male member 147 is coupled to the inner member 122.

Such coupling can allow the male member 147 to displace (e.g., longitudinally) the inner member 122 without substantially rotating or applying torque on the inner member 122. For example, the spherical portion 137 may be configured to rotate within at least a portion of the male member 147 (e.g., within a substantially spherical cavity). The male member 147 can include a proximal threaded portion 177 and a distal portion 179. The distal portion 179 can include a first surface 180*a* and a second surface 180*b*. As illustrated, the distal portion 179 can be at least partially disposed in a proximal channel 167 of the grip portion 140, wherein each of the first and second surfaces 180*a*, 180*b* can be substantially planar or flat. In certain embodiments, an engagement or interaction between the first and second surfaces 180*a*, 180*b* of the male member 147 and at least a portion of an inner surface of the proximal channel 167 can prevent or restrict the male member 147 from rotating relative to the grip portion 140.

A plurality of threads 178 can be disposed on at least a portion of the proximal threaded portion 177 of the male member 147. The female member 144 can further include an inner cavity 182, and a plurality of threads 183 can be disposed on at least a portion of a surface of the inner cavity 182. The plurality of threads 178 of the male member 147 can be configured to engage or interact (e.g., threadably engage or interact) with the plurality of the threads 183 of the female member 144.

In various embodiments, upon actuation or rotation of the actuator portion 142, the male member 147 may be displaced or linearly displaced (e.g., proximally or distally) relative to the female member 144 due at least in part to threaded engagement between each of the male member 147 and the female member 144. Such a configuration can allow a user to impart a substantially large force on at least a subset of the components disposed within the handle 115 (e.g., due to translation of force from the actuator portion 142 to the female member 144 and other components that may be operably coupled to the female member 144).

During actuation of the actuator portion 142 in a first direction, the male member 147 can be displaced proximally in relation to the grip portion 140. Proximal displacement of the male member 147 can result in or effect proximal displacement of the inner member 122 in relation to the outer member 120. Further, proximal displacement of the inner member 122 in relation to the outer member 120 can result in bending, curving, and/or deflection of the working end portion 110 as the inner member 122 is coupled to the outer member 120 at the coupling portion 160.

In some embodiments, for example, if the distal end 113 of the working end portion 110 is restrained within a rigid cannula or hard bone, deflection of the working end portion 110 may be inhibited or prevented. At full deflection, or substantially full deflection, of the working end portion 110, a proximal end of the proximal threaded portion 177 of the male member 147 may abut, or be configured to abut, a portion of the surface of the inner cavity 182 of the female member 144 (e.g., the male member 147 may hit a hard stop).

If, for example, the distal end 113 of the working end portion 110 is restrained within a cannula or hard bone, and if full deflection has not been achieved, the male member 147 may still be displaceable within the female member 144. For example, there may still be a gap between the proximal end of the proximal threaded portion 177 of the male member 147 and the surface of the inner cavity 182 of the female member 144. Accordingly, the male member 147 may have a potential distance to travel or be displaced. If the user continues to rotate the actuator portion 142 in this configuration (i.e., a non-fully deflected configuration), the holding power of the resilient arms 143 may be exceeded (due to resistance to bending of the working portion 110 due to its position within the bone), one or more of the resilient arms 143 may be pushed radially outward, and the one or more teeth 173 may be displaced or slip over one or more of the ridges 145. For example, a tooth 173 may be displaced from a first groove 146 to an adjacent groove 146 (e.g., a second groove 146). Furthermore, the tooth 173 may be displaced from a first groove 146 to a third groove 146, a fourth groove 146, etc.

The resilient arms 143 and the ridges 145 and/or the grooves 146 can interact analogously whether the actuator portion 142 is being rotated clockwise or counter-clockwise (e.g., by a user). In certain embodiments, a cross-section of the resilient arms 143 may be thicker or thinner than the illustrated resilient arms 143. In some embodiments, the resilient arms 143 may be shorter or longer than the illustrated resilient arms 143. Such adjustments or modifications to the configuration of the resilient arms 143 can be used to select a desired force (e.g., a release force) at which the resilient arms 143 extend radially outward and release torque on at least a subset of the components of the handle 115. In various embodiments, the release force may be greater than a force required to deflect the working end portion 110. In certain embodiments, the release force may be less than a force that may result in damage to at least a portion of the male member 147 and/or the female member 144.

The coupling of the female member 144 and the actuator portion 142 as described above may be configured to prevent a user from exerting an excessive amount of torque on the extension member 105, which could potentially damage one or more components (e.g., the inner member 122 or the male member 147) of the medical device 100. For example, in some embodiments, the plurality of teeth 173 that project radially inward from the resilient arms 143 may be configured to deflect outward when too much torque is provided, thereby causing the actuator portion 142 to disengage from the ridges 145 and/or the grooves 146 on the female member 144. More particularly, at a selected torque—for example, a torque that is greater than about 6 inch-pounds but less than about 16 inch-pounds—the actuator portion 142 may disengage from the ridges 145 and/or the grooves 146 on the female member 144. Such disengagement can prevent the user from exerting an excessive amount of force on the medical device 100. Stated differently, the actuator portion 142 may function as a torque limiter and/or release system.

Furthermore, such disengagement can prevent the spherical portion 137 from being displaced, breaking, and/or extruding through a distal end of the male member 147. Such disengagement can also prevent or restrict the threads 178 of the male member 147 and/or the threads 183 of the female member 144 from failing or being stripped. Accordingly, proper functioning of the medical device 100 can be maintained.

As discussed above, the medical device 100 may be configured for treating a hard tissue. In some embodiments, the medical device 100 can include the extension member 105, wherein the extension member 105 includes the inner member 122 disposed within at least a portion of the outer member 120. The handle 115 can be releasably coupled to the extension member 105. In certain embodiments, actuation (e.g., rotation) of the handle 115 can be configured to transition the working end portion 110 of the extension member 105 between the deflected configuration and the undeflected configuration. Furthermore, a torque release mechanism can be coupled to each of the handle 115 and the inner member 122. In various embodiments, the torque release mechanism can be configured to transition the medical device 100 between a torque release configuration and a torque retention configuration (as described in further detail below).

In various embodiments, the handle 115 can include the actuator portion 142, wherein the actuator portion 142 can be releasably coupled to the inner member 122. The handle 115 can also include a grip portion 140, wherein the grip portion 140 is disposed distally of and is rotatably coupled to the actuator portion 142. Furthermore, the grip portion 140 can be releasably coupled to the outer member 120. In some embodiments, the medical device 100 may include more than one torque release mechanisms. For example, a first or proximal torque release mechanism may be coupled to each of the actuator portion 142 and the inner member 122. The proximal torque release mechanism may be configured to transition the inner member 122 between a torque release configuration (e.g., a proximal torque release configuration) and a torque retention configuration (e.g., a proximal torque retention configuration). Additionally, a second or distal torque release mechanism may be coupled to each of the grip portion 140 and the outer member 120. The distal torque release mechanism may be configured to transition the outer member 120 between a torque release configuration (e.g., a distal torque release configuration) and a torque retention configuration (e.g., a distal torque retention configuration).

The torque release mechanism can further be configured to uncouple the inner member 122 from the handle 115 when an amount of torque applied to the handle 115 exceeds a predetermined value. For example, the torque release mechanism may be configured to limit or prevent damage to the medical device 100 (e.g., due to the application of excessive force to the handle 115 and/or the medical device 100). In some embodiments, the proximal torque release mechanism may be configured to uncouple the inner member 122 from the actuator portion 142 when an amount of torque applied to the actuator portion 142 exceeds a first predetermined value. Furthermore, the distal torque release mechanism may be configured to uncouple the outer member 120 from the grip portion 140 when an amount of torque applied to the outer member 120 exceeds a second predetermined value.

In some embodiments, torque may be transferred between the handle 115 and the extension member 105 via the torque release mechanism, or the proximal torque release mechanism, when the medical device 100 and/or the torque release mechanism is in the torque retention configuration. In contrast, torque may not be transferred between the handle 115 and the extension member 105 via the torque release mechanism, or the proximal torque release mechanism, when the medical device 100 and/or the torque release mechanism is in the torque release configuration.

The handle 115 can include the actuator portion 142, wherein the actuator portion 142 can be releasably coupled to the working end portion 110 at least via the inner member 122. In certain embodiments, actuation of the actuator portion 142 may be configured to longitudinally displace the inner member 122 relative to the outer member 120. Such displacement can transition the working end portion 110 between the deflected configuration and the undeflected configuration.

A first portion of the torque release mechanism, or the proximal torque release mechanism, may be disposed within the actuator portion 142, and a second portion of the torque release mechanism, or the proximal torque release mechanism, may be coupled to the proximal end 134 of the inner member 122. Furthermore, the first and second portions of the torque release mechanism, or the proximal torque release mechanism, may be releasably coupled to each other.

In various embodiments, the first portion of the torque release mechanism, or the proximal torque release mechanism, may include at least one tooth 173 extending radially inward from the inside surface of the actuator portion 142. The second portion of the torque release mechanism, or the proximal torque release mechanism, may include at least one groove 146 extending radially inward from an outside surface of the female member 144. The at least one groove 146 (i.e., of the second portion of the torque release mechanism or the proximal torque release mechanism) can be configured to engage the at least one tooth 173 (i.e., of the first portion of the torque release mechanism or the proximal torque release mechanism).

In some embodiments, the at least one tooth 173 can be coupled to the resilient arm 143, wherein the resilient arm 143 extends radially inward from at least a portion of the inside surface of the actuator portion 142. A distal portion of the resilient arm 143 may be displaced radially outward relative to a longitudinal axis of the actuator portion 142 when the medical device 100 and/or the torque release mechanism is in the torque release configuration. Such displacement of at least a portion of the resilient arm 143 can disengage the at least one tooth 173 from the at least one groove 146.

As described above, the medical device 100 can further include the male member 147. The male member 147 can be coupled to the proximal end 134 of the inner member 122. Additionally, the male member 147 can be threadably engaged with the female member 144 such that actuation (e.g., rotation) of the female member 144 can longitudinally displace the male member 147 relative to the female member 144.

Actuation of the actuator portion 142 can be configured to engage, or result in the engagement of, the at least one tooth 173 with the at least one groove 146. Such engagement may result in actuation of the female member 144 when the medical device 100 is in the torque retention configuration. Furthermore, actuation of the female member 144 may be configured to longitudinally displace the inner member 122 relative to the outer member 120. In certain embodiments, the at least one tooth 173 may be configured to be disengaged from the at least one groove 146 when the medical device 100 is in the torque release configuration. In such a configuration (e.g., wherein the at least one tooth 173 is disengaged from the at least one groove 146), actuation of the actuation portion 142 may not actuate or result in actuation of the female member 144. As stated above, actuation of the actuator portion 142 may include rotation of at least a portion of the actuator portion 142. Likewise, actuation of the female member 144 may include rotation of at least a portion of the female member 144. When the medical device 100 is in the torque release configuration, the actuator portion 142 can be uncoupled from at least the extension member 105 such that actuation of the actuator portion 142 does not deflect the working end portion 110.

Methods of using the medical devices or osteotomes (e.g., the medical device 100) are also disclosed herein. In some aspects, the present disclosure is directed to methods of treating a hard tissue (e.g., a bone) of a patient or subject. In some embodiments, the methods can include obtaining the medical device (such as the medical device or osteotome 100). The medical device, as described above, can include an outer member and an inner member disposed within a portion of the outer member. Furthermore, a distal end of the outer member can be coupled to (e.g., fixedly coupled to) a distal end of the inner member. The distal end portions of the outer and inner members can form a working end portion.

In certain embodiments, the methods of treating the hard tissue can further include advancing the working end portion of the medical device into at least a portion of the hard tissue of the patient. The working end portion can be advanced in a first direction. In various embodiments, the methods can further include actuating the medical device (e.g., via a handle) to longitudinally displace the inner member relative to the outer member. Accordingly, a plurality of slots disposed along the distal end portion of the outer member and a recessed portion disposed along the distal end portion of the inner member can interact to transition the working end portion from an undeflected configuration to a deflected configuration.

In some embodiments, the methods of treating the hard tissue of the patient can further include observing a disposition or direction of an indicator operably coupled to the outer member. Such observation can be used to determine a direction (e.g., the first direction) of the deflection of the working end portion. Upon observation of the disposition of the indicator, the user may desire to adjust a direction of the deflection relative to the hard tissue being treated. Accordingly, the user can adjust the medical device to advance the working end portion in a second direction (e.g., based at least in part on the direction of the deflection communicated by the indicator).

In certain embodiments, the methods of treating the hard tissue of the patient can include obtaining a medical device as described herein (e.g., medical device 100). As discussed above, the medical device can include an outer member and an inner member disposed within at least a portion of the outer member. Distal end portions of each of the outer and inner members may cooperate to form a working end portion. Furthermore, a handle can be releasably coupled to the working end portion.

The methods of treating the hard tissue of the patient can further include advancing the working end portion into the hard tissue of the patient. A practitioner or user may actuate at least a portion of the handle to transition the working end portion between an undeflected configuration and a deflected configuration. Furthermore, the practitioner may apply torque to the handle. In certain embodiments, the level of torque applied to the handle may exceed a predetermined value. Accordingly, further actuation of the handle may uncouple the handle from the working end portion (e.g., via a torque release mechanism).

In various embodiments, the practitioner may decrease an amount of torque applied to the handle such that the handle is recoupled to, or recouples, the working end portion. In various other embodiments, the practitioner may cease or stop applying torque to the handle such that the handle is recoupled to, or recouples, the working end portion. Additionally, the practitioner may adjust a position of the working end portion (e.g., within the hard tissue). Accordingly, the amount of torque applied to the medical device may be decreased. The practitioner may then actuate the handle to further transition the working end portion between the undeflected configuration and the deflected configuration.

As can be appreciated by one of skill in the art having the benefit of this disclosure, additional methods and/or method steps can be derived from FIGS. 1-8B and the corresponding disclosure. Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially circular" is recited with respect to a feature, it is understood that in further embodiments, the feature can have a precisely circular configuration.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, which changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A medical device for treating a hard tissue, the medical device comprising:
   a handle;
   an extension member operably coupled to the handle, the extension member comprising an inner member disposed within an outer member, wherein actuation of the handle is configured to deflect a working end portion of the extension member, the working end portion disposed adjacent a distal end of the extension member; and an indicator operably coupled to the outer member, wherein the indicator communicates a direction of deflection of the working end portion to a user;

wherein the indicator comprises:

an elongate body;

a locking member coupled to a proximal end of the elongate body, the locking member configured to operably couple the indicator to the outer member; and an indicator arm coupled to a distal end of the elongate body, the indicator arm extending radially outward from a longitudinal axis of the elongate body, and the indicator arm configured to communicate the direction of deflection of the working end portion to the user.

2. The medical device of claim 1, wherein the handle comprises:

an actuator portion operably coupled to the working end portion; and a grip portion disposed distal of and operably coupled to the actuator portion, wherein actuation of the actuator portion is configured to longitudinally displace the inner member relative to the outer member such that the working end portion transitions between a deflected configuration and an undeflected configuration.

3. The medical device of claim 2, wherein the locking member of the indicator is disposed within the grip portion, and wherein the indicator arm is disposed outside of the grip portion such that the indicator arm is visible to the user.

4. The medical device of claim 1, further comprising a distal collar disposed within and coupled to the handle, the distal collar comprising:

an outer member receiving portion configured to couple a proximal end of the outer member to the distal collar; and a locking member receiving portion configured to couple a proximal end of the indicator to the distal collar.

5. The medical device of claim 4, wherein a locking member is coupled to the proximal end of the indicator, the locking member comprising at least one extension extending radially outward from a longitudinal axis of the indicator, the at least one extension configured to engage the locking member receiving portion such that the indicator is not rotatable relative to the distal collar.

6. A medical device for treating a hard tissue, the medical device comprising:

a handle; and an extension member coupled to the handle, the extension member comprising:

an outer member comprising a lumen extending from a distal end of the outer member and a plurality of slots disposed in a wall of the outer member along a distal end portion of the outer member; and an inner member disposed within a portion of the outer member, the inner member comprising a recessed portion along a distal end portion of the inner member, the distal end portions of the outer and inner members forming a working end portion of the extension member;

wherein the plurality of slots are circumferentially offset from the recessed portion, and wherein the plurality of slots and the recessed portion interact to permit deflection of the working end portion upon actuation of the handle.

7. The medical device of claim 6, wherein the distal end of the outer member is fixedly coupled to the distal end of the inner member.

8. The medical device of claim 6, wherein actuation of the handle longitudinally displaces the inner member relative to the outer member to transition the working end portion from an undeflected configuration to a deflected configuration.

9. The medical device of claim 6, wherein the plurality of slots substantially limit deflection of the working end portion to a single plane.

10. The medical device of claim 6, wherein a length of the recessed portion is substantially equal to a length of a portion of the outer member comprising the plurality of slots.

11. The medical device of claim 6, wherein a length of the recessed portion is greater than a length of a portion of the outer member comprising the plurality of slots.

12. The medical device of claim 6, wherein a length of the recessed portion is less than a length of a portion of the outer member comprising the plurality of slots.

13. The medical device of claim 6, wherein the inner member comprises a wire, and wherein a thickness of the wire distal and proximal of the recessed portion is greater than a thickness of the wire at the recessed portion.

14. The medical device of claim 6, wherein the recessed portion comprises a distal end, a medial portion, and a proximal end, the medial portion having a first thickness, a portion of the inner member disposed proximal of the recessed portion having a second thickness, and a portion of the inner member disposed distal of the recessed portion having a third thickness, wherein the second and third thicknesses are greater than the first thickness.

15. The medical device of claim 14, wherein a thickness of the inner member transitions from the first thickness to the second thickness at the proximal end of the recessed portion, and wherein the thickness of the inner member transitions from the first thickness to the third thickness at the distal end of the recessed portion.

16. The medical device of claim 15, wherein at least one reinforcement member is disposed within the recessed portion.

17. The medical device of claim 15, wherein a cross-section transverse to a longitudinal axis of the inner member at a position proximal of the recessed portion is substantially circular, and wherein a cross-section transverse to the longitudinal axis of the inner member at the recessed portion is substantially segmental.

18. A medical device for treating a hard tissue, the medical device comprising:

a handle;

an extension member operably coupled to the handle, the extension member comprising an inner member disposed within an outer member, wherein actuation of the handle is configured to deflect a working end portion of the extension member, the working end portion disposed adjacent a distal end of the extension member; and an indicator operably coupled to the outer member, wherein the indicator communicates a direction of deflection of the working end portion to a user;

a distal collar disposed within and coupled to the handle, the distal collar comprising:

an outer member receiving portion configured to couple a proximal end of the outer member to the distal collar; and a locking member receiving portion configured to couple a proximal end of the indicator to the distal collar.

19. The medical device of claim 18, wherein a locking member is coupled to the proximal end of the indicator, the locking member comprising at least one extension extending radially outward from a longitudinal axis of the indicator, the at least one extension configured to engage the locking member receiving portion such that the indicator is not rotatable relative to the distal collar.

* * * * *